(12) United States Patent
Penny et al.

(10) Patent No.: US 6,479,236 B2
(45) Date of Patent: *Nov. 12, 2002

(54) GENOTYPING THE HUMAN UDP-GLUCURONOSYLTRANSFERASE 1 (UGT1) GENE

(75) Inventors: Laura Penny, San Diego, CA (US); Margaret Galvin, Carlsbad, CA (US)

(73) Assignee: DNA Sciences Laboratories, Inc., Morrisville, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 1 days.

(21) Appl. No.: 09/305,856

(22) Filed: May 5, 1999

(65) Prior Publication Data

US 2002/0061518 A1 May 23, 2002

Related U.S. Application Data

(60) Provisional application No. 60/084,807, filed on May 7, 1998.

(51) Int. Cl.$^7$ ............................. C07H 21/04; C12Q 1/68
(52) U.S. Cl. .......................... 435/6; 536/23.1; 536/24.3; 536/24.31
(58) Field of Search .......................... 435/6; 536/23.1, 536/24.3, 24.31

(56) References Cited

U.S. PATENT DOCUMENTS 5,736,387 A * 4/1998 Vogelstein et al. ........ 435/320.1

FOREIGN PATENT DOCUMENTS

| WO | WO 92/12987 | 8/1992 |
|---|---|---|
| WO | WO 97/32042 | 9/1997 |

OTHER PUBLICATIONS

Cho et al (Genbank Accession No. U42604, Feb. 2, 1996).*
Ritter et al (Genbank Accession No. M84127, Mar. 1996).*
Ritter et al (Genbank Accession No. M84128, Jan. 1995).*
Ritter et al (Genbank Accession No. M84126, Jan. 1995).*
Genbank Attachment #1: sequence search results.*
Genbank Attachment #2: pertinant sequences.*
Koiwai et al. "Gilbert's syndrome is caused by a heterozygous missense mutation in the gene for bilirubin UDP–glucuronosyltransferase". Hum. Mol. Genetics, vol. 4, No. 7, pp. 1183–1186, Jul. 1995.*
Ritter et al "Cloning of two human liver bilirubin UDP–glucuronolsyltransferase cDNAs with expression inCOS–1 cells." J. of Bio. Chem. vol. 266, No. 2, pp. 1043–4017, Jan. 1991.*
Aono et al. "Analysis of genes for bilirubin UDP–glucuronosyltransferase in Gilbert's syndrome" The Lancet, vol. 345, pp. 958–959, Apr. 15, 1995.*
Cronin et al. "Cystic Fibrosis mutation detection by hybridization to light–generated DNA probe arrays" Human Mutation, Vil 7, pp. 244, 255, 1996.*
Strassburg et al "Differential expression of the UGT1A locus in human liver, Biliary, and gastric tissue" Molecular Pharmacology, vol. 52, pp. 212–220, 1997.*
Ciotti et al "Genetic polymorphism in the human UGT1A UDP–Glucuronosyltransferase" Am J. of Human Genetics, vol. 61, No. 4, pp. 1149, OCt. 1997.*
Yamamoto et al. "Analysis of bilirubin uridine 5'–diphosphate (UDP–glucuronosyltransferase gene mutations in seven patients with Crigler–Najjar syndrome type II" J. Hum. Genet, vol. 43, pp. 111–114, 1998.*
Flores–Diaz et al. "Cellular UDP–glucose Deficiency caused by a single point mutation in the UDP–glucose pyrophosphorylase gene" J. of Biological Chemistry, vol. 272, No. 38, pp. 23784–23791, Sep. 1997.*
Koiwai et al. "Crigler–Najjar syndrome type II is inherited both as a dominant and as a recessive trait"Human Molecular Genetic, vol. 5, No. 5, pp. 645–647, 1996.*
Aono et al. "A new type of defect in the gene for bilirubin uridine 5'diphosphate–glucuronosyltransferase in a patient with crigler–Najjar syndrom Type I" Pediatric Research, vol. 35, No. 6, pp. 629–632, 1994.*
Labrune et al "Genetic heterogeneitiy of Crigler–Najjar syndrom type I: a study of 14 cases" Human Genetics, vol. 94, pp. 693–697, 1994.*
Daly et al. "Metabolic polymorphisms" Pharmac. Ther. vol. 57, pp. 129–160, 1993.*
GenBank Alignment Packet #2.*
GenBank Accession No. M84122.
GenBank Accession No. M84123.
GenBank Accession No. M84124.
NCBI Entrez Accession No. M84125.
NCBI Entrez Accession No. M84127.
NCBI Entrez Accession No. M84128.
NCBI Entrez Accession No. M84129.
NCBI Entrez Accession No. M84130.
NCBI Entrez Accession No. U39550.
NCBI Entrez Accession No. U42604.
OMIM Entry 191740.
OMIM Entry 218800.
NCBI Entrez Accession No. M84130.
Bosma et al., *New Eng. J. Med.*, 333(18):1171–1175 (1995).

(List continued on next page.)

*Primary Examiner*—Lisa B. Arthur
*Assistant Examiner*—Jeanine Goldberg
(74) *Attorney, Agent, or Firm*—Sheridan Ross P.C.

(57) ABSTRACT

Genetic polymorphisms are identified in the human UGT1 gene that alter UGT1-dependent drug metabolism. Nucleic acids comprising the polymorphic sequences are used to screen patients for altered metabolism for UGT1 substrates, potential drug-drug interactions, and adverse/side effects, as well as diseases that result from environmental or occupational exposure to toxins. The nucleic acids are used to establish animal, cell and in vitro models for drug metabolism.

10 Claims, 3 Drawing Sheets

OTHER PUBLICATIONS

Burchell et al., *Life Sciences*, 57(20):1819–1831 (1995).
Ciotti et al., *Pharmacogenetics*, 7:485–495 (1997).
Iwano et al., *Biochem. J.*, 325:587–591 (1997).
Mackenzie et al., *Pharmacogenetics*, 7:255–269 (1997).
Miners et al., *Pharmac. Ther.*, 51:347–369 (1991).
Monaghan et al., *Lancet*, 347:578–581 (1996).
Owens et al., *Pharmacogenetics*, 2:93–108 (1992).
Ritter et al., *J. Biological Chem.*, 267(5):3257–3261 (1992).

* cited by examiner

SEQUENCE LISTING

<160> NUMBER OF SEQ ID NOS: 124

<210> SEQ ID NO 1
<211> LENGTH: 864
<212> TYPE: DNA
<213> ORGANISM: Homo sapiens
<220> FEATURE:
<221> NAME/KEY: CDS
<222> LOCATION: (1)...(864)

<400> SEQUENCE: 1

```
atg gct gtg gag tcc cag ggc gga cgc cca ctt gtc ctg ggc ctg ctg      48
Met Ala Val Glu Ser Gln Gly Gly Arg Pro Leu Val Leu Gly Leu Leu
 1               5                  10                  15 ctg tgt gtg ctg ggc cca gtg gtg tcc cat gct ggg aag ata ctg ttg      96
Leu Cys Val Leu Gly Pro Val Val Ser His Ala Gly Lys Ile Leu Leu
             20                  25                  30 atc cca gtg gat ggc agc cac tgg ctg agc atg ctt ggg gcc atc cag     144
Ile Pro Val Asp Gly Ser His Trp Leu Ser Met Leu Gly Ala Ile Gln
         35                  40                  45 cag ctg cag cag agg gga cat gaa ata gtt gtc cta gca cct gac gcc     192
Gln Leu Gln Gln Arg Gly His Glu Ile Val Val Leu Ala Pro Asp Ala
     50                  55                  60 tcg ttg tac atc aga gac gga gca ttt tac acc ttg aag acg tac cct     240
Ser Leu Tyr Ile Arg Asp Gly Ala Phe Tyr Thr Leu Lys Thr Tyr Pro
 65                  70                  75                  80 gtg cca ttc caa agg gag gat gtg aaa gag tct ttt gtt agt ctc ggg     288
Val Pro Phe Gln Arg Glu Asp Val Lys Glu Ser Phe Val Ser Leu Gly
                 85                  90                  95 cat aat gtt ttt gag aat gat tct ttc ctg cag cgt gtg atc aaa aca     336
His Asn Val Phe Glu Asn Asp Ser Phe Leu Gln Arg Val Ile Lys Thr
            100                 105                 110 tac aag aaa ata aaa aag gac tct gct atg ctt ttg tct ggc tgt tcc     384
Tyr Lys Lys Ile Lys Lys Asp Ser Ala Met Leu Leu Ser Gly Cys Ser
        115                 120                 125 cac tta ctg cac aac aag gag ctc atg gcc tcc ctg gca gaa agc agc     432
His Leu Leu His Asn Lys Glu Leu Met Ala Ser Leu Ala Glu Ser Ser
    130                 135                 140 ttt gat gtc atg ctg acg gac cct ttc ctt cct tgc agc ccc atc gtg     480
Phe Asp Val Met Leu Thr Asp Pro Phe Leu Pro Cys Ser Pro Ile Val
145                 150                 155                 160 gcc cag tac ctg tct ctg ccc act gta ttc ttc ttg cat gca ctg cca     528
Ala Gln Tyr Leu Ser Leu Pro Thr Val Phe Phe Leu His Ala Leu Pro
                165                 170                 175 tgc agc ctg gaa ttt gag gct acc cag tgc ccc aac cca ttc tcc tac     576
Cys Ser Leu Glu Phe Glu Ala Thr Gln Cys Pro Asn Pro Phe Ser Tyr
            180                 185                 190 gtg ccc agg cct ctc tcc tct cat tca gat cac atg acc ttc ctg cag     624
Val Pro Arg Pro Leu Ser Ser His Ser Asp His Met Thr Phe Leu Gln
        195                 200                 205 cgg gtg aag aac atg ctc att gcc ttt tca cag aac ttt ctg tgc gac     672
```

-continued

```
Arg Val Lys Asn Met Leu Ile Ala Phe Ser Gln Asn Phe Leu Cys Asp
    210                 215                 220 gtg gtt tat tcc ccg tat gca acc ctt gcc tca gaa ttc ctt cag aga    720
Val Val Tyr Ser Pro Tyr Ala Thr Leu Ala Ser Glu Phe Leu Gln Arg
225                 230                 235                 240 gag gtg act gtc cag gac cta ttg agc tct gca tct gtc tgg ctg ttt    768
Glu Val Thr Val Gln Asp Leu Leu Ser Ser Ala Ser Val Trp Leu Phe
                245                 250                 255 aga agt gac ttt gtg aag gat tac cct agg ccc atc atg ccc aat atg    816
Arg Ser Asp Phe Val Lys Asp Tyr Pro Arg Pro Ile Met Pro Asn Met
            260                 265                 270 gtt ttt gtt ggt gga atc aac tgc ctt cac caa aat cca cta tcc cag    864
Val Phe Val Gly Gly Ile Asn Cys Leu His Gln Asn Pro Leu Ser Gln
        275                 280                 285
```

<210> SEQ ID NO 2
<211> LENGTH: 288
<212> TYPE: PRT
<213> ORGANISM: Homo sapiens

<400> SEQUENCE: 2

```
Met Ala Val Glu Ser Gln Gly Gly Arg Pro Leu Val Leu Gly Leu Leu
1               5                   10                  15

Leu Cys Val Leu Gly Pro Val Val Ser His Ala Gly Lys Ile Leu Leu
                20                  25                  30

Ile Pro Val Asp Gly Ser His Trp Leu Ser Met Leu Gly Ala Ile Gln
            35                  40                  45

Gln Leu Gln Gln Arg Gly His Glu Ile Val Val Leu Ala Pro Asp Ala
        50                  55                  60

Ser Leu Tyr Ile Arg Asp Gly Ala Phe Tyr Thr Leu Lys Thr Tyr Pro
65                  70                  75                  80

Val Pro Phe Gln Arg Glu Asp Val Lys Glu Ser Phe Val Ser Leu Gly
                85                  90                  95

His Asn Val Phe Glu Asn Asp Ser Phe Leu Gln Arg Val Ile Lys Thr
                100                 105                 110

Tyr Lys Lys Ile Lys Lys Asp Ser Ala Met Leu Leu Ser Gly Cys Ser
            115                 120                 125

His Leu Leu His Asn Lys Glu Leu Met Ala Ser Leu Ala Glu Ser Ser
        130                 135                 140

Phe Asp Val Met Leu Thr Asp Pro Phe Leu Pro Cys Ser Pro Ile Val
145                 150                 155                 160

Ala Gln Tyr Leu Ser Leu Pro Thr Val Phe Phe Leu His Ala Leu Pro
                165                 170                 175

Cys Ser Leu Glu Phe Glu Ala Thr Gln Cys Pro Asn Pro Phe Ser Tyr
            180                 185                 190

Val Pro Arg Pro Leu Ser Ser His Ser Asp His Met Thr Phe Leu Gln
        195                 200                 205

Arg Val Lys Asn Met Leu Ile Ala Phe Ser Gln Asn Phe Leu Cys Asp
    210                 215                 220

Val Val Tyr Ser Pro Tyr Ala Thr Leu Ala Ser Glu Phe Leu Gln Arg
225                 230                 235                 240

Glu Val Thr Val Gln Asp Leu Leu Ser Ser Ala Ser Val Trp Leu Phe
                245                 250                 255

Arg Ser Asp Phe Val Lys Asp Tyr Pro Arg Pro Ile Met Pro Asn Met
            260                 265                 270

Val Phe Val Gly Gly Ile Asn Cys Leu His Gln Asn Pro Leu Ser Gln
```

<210> SEQ ID NO 3
<211> LENGTH: 867
<212> TYPE: DNA
<213> ORGANISM: Homo sapiens
<220> FEATURE:
<221> NAME/KEY: CDS
<222> LOCATION: (1)...(867)

<400> SEQUENCE: 3

| | | | | | | | | | | | | | | | | |
|---|---|---|---|---|---|---|---|---|---|---|---|---|---|---|---|---|
| atg | gcc | aca | gga | ctc | cag | gtt | ccc | ctg | ccg | tgg | ctg | gcc | aca | gga | ctg | 48 |
| Met | Ala | Thr | Gly | Leu | Gln | Val | Pro | Leu | Pro | Trp | Leu | Ala | Thr | Gly | Leu | |
| 1 | | | | 5 | | | | | 10 | | | | | 15 | | |
| ctg | ctt | ctc | ctc | agt | gtc | cag | ccc | tgg | gct | gag | agt | gga | aag | gtg | ttg | 96 |
| Leu | Leu | Leu | Leu | Ser | Val | Gln | Pro | Trp | Ala | Glu | Ser | Gly | Lys | Val | Leu | |
| | | | 20 | | | | | 25 | | | | | 30 | | | |
| gtg | gtg | ccc | att | gat | ggc | agc | cac | tgg | ctc | agc | atg | cgg | gag | gtc | ttg | 144 |
| Val | Val | Pro | Ile | Asp | Gly | Ser | His | Trp | Leu | Ser | Met | Arg | Glu | Val | Leu | |
| | | 35 | | | | | 40 | | | | | 45 | | | | |
| cgg | gag | ctc | cat | gcc | aga | ggc | cac | cag | gca | gtg | gtc | ctc | acc | cca | gag | 192 |
| Arg | Glu | Leu | His | Ala | Arg | Gly | His | Gln | Ala | Val | Val | Leu | Thr | Pro | Glu | |
| | 50 | | | | | 55 | | | | | 60 | | | | | |
| gtg | aat | atg | cac | atc | aaa | gaa | gag | aac | ttt | ttc | acc | ctg | aca | acc | tat | 240 |
| Val | Asn | Met | His | Ile | Lys | Glu | Glu | Asn | Phe | Phe | Thr | Leu | Thr | Thr | Tyr | |
| 65 | | | | 70 | | | | | 75 | | | | | 80 | | |
| gcc | att | tcg | tgg | acc | cag | gat | gaa | ttt | gat | cgc | cat | gtg | ctg | ggc | cac | 288 |
| Ala | Ile | Ser | Trp | Thr | Gln | Asp | Glu | Phe | Asp | Arg | His | Val | Leu | Gly | His | |
| | | | 85 | | | | | 90 | | | | | 95 | | | |
| act | caa | ctg | tac | ttt | gaa | aca | gaa | cat | ttt | ctg | aag | aaa | ttt | ttc | aga | 336 |
| Thr | Gln | Leu | Tyr | Phe | Glu | Thr | Glu | His | Phe | Leu | Lys | Lys | Phe | Phe | Arg | |
| | | | 100 | | | | | 105 | | | | | 110 | | | |
| agt | atg | gca | atg | ttg | aac | aat | atg | tct | ttg | gtc | tat | cat | agg | tct | tgt | 384 |
| Ser | Met | Ala | Met | Leu | Asn | Asn | Met | Ser | Leu | Val | Tyr | His | Arg | Ser | Cys | |
| | 115 | | | | | 120 | | | | | 125 | | | | | |
| gtg | gag | cta | cta | cat | aat | gag | gcc | ctg | atc | agg | cac | ctg | aat | gct | act | 432 |
| Val | Glu | Leu | Leu | His | Asn | Glu | Ala | Leu | Ile | Arg | His | Leu | Asn | Ala | Thr | |
| 130 | | | | | 135 | | | | | 140 | | | | | | |
| tcc | ttt | gat | gtg | gtt | tta | aca | gac | ccc | gtt | aac | ctc | tgc | gcg | gca | gtg | 480 |
| Ser | Phe | Asp | Val | Val | Leu | Thr | Asp | Pro | Val | Asn | Leu | Cys | Ala | Ala | Val | |
| 145 | | | | 150 | | | | | 155 | | | | | 160 | | |
| ctg | gct | aag | tac | ctg | tcg | att | cct | act | gtg | ttt | ttt | ttg | agg | aac | att | 528 |
| Leu | Ala | Lys | Tyr | Leu | Ser | Ile | Pro | Thr | Val | Phe | Phe | Leu | Arg | Asn | Ile | |
| | | | 165 | | | | | 170 | | | | | 175 | | | |
| cca | tgt | gat | tta | gac | ttt | aag | ggc | aca | cag | tgt | cca | aac | cct | tcc | tcc | 576 |
| Pro | Cys | Asp | Leu | Asp | Phe | Lys | Gly | Thr | Gln | Cys | Pro | Asn | Pro | Ser | Ser | |
| | | | 180 | | | | | 185 | | | | | 190 | | | |
| tat | att | cct | aga | tta | cta | aca | acc | aat | tca | gac | cac | atg | aca | ttc | atg | 624 |
| Tyr | Ile | Pro | Arg | Leu | Leu | Thr | Thr | Asn | Ser | Asp | His | Met | Thr | Phe | Met | |
| | 195 | | | | | 200 | | | | | 205 | | | | | |
| caa | agg | gtc | aag | aac | atg | ctc | tac | cct | ctg | gcc | ctg | tcc | tac | att | tgc | 672 |
| Gln | Arg | Val | Lys | Asn | Met | Leu | Tyr | Pro | Leu | Ala | Leu | Ser | Tyr | Ile | Cys | |
| 210 | | | | | 215 | | | | | 220 | | | | | | |
| cat | gct | ttt | tct | gct | cct | tat | gca | agc | ctt | gcc | tct | gag | ctt | ttt | cag | 720 |
| His | Ala | Phe | Ser | Ala | Pro | Tyr | Ala | Ser | Leu | Ala | Ser | Glu | Leu | Phe | Gln | |
| 225 | | | | | 230 | | | | | 235 | | | | | 240 | |
| aga | gag | gtg | tca | gtg | gtg | gat | att | ctc | agt | cat | gca | tct | gtg | tgg | ctg | 768 |
| Arg | Glu | Val | Ser | Val | Val | Asp | Ile | Leu | Ser | His | Ala | Ser | Val | Trp | Leu | |
| | | | 245 | | | | | 250 | | | | | 255 | | | |
| ttc | cga | ggg | gac | ttt | gtg | atg | gac | tac | ccc | agg | cca | atc | atg | ccc | aac | 816 |
| Phe | Arg | Gly | Asp | Phe | Val | Met | Asp | Tyr | Pro | Arg | Pro | Ile | Met | Pro | Asn | |

```
atg gtc ttc att ggg ggc atc aac tgt gcc aac agg aag cca cta tct    864
Met Val Phe Ile Gly Gly Ile Asn Cys Ala Asn Arg Lys Pro Leu Ser
        275                 280                 285 cag                                                                867
Gln
```

<210> SEQ ID NO 4
<211> LENGTH: 289
<212> TYPE: PRT
<213> ORGANISM: Homo sapiens

<400> SEQUENCE: 4

```
Met Ala Thr Gly Leu Gln Val Pro Leu Pro Trp Leu Ala Thr Gly Leu
 1               5                  10                  15

Leu Leu Leu Leu Ser Val Gln Pro Trp Ala Glu Ser Gly Lys Val Leu
            20                  25                  30

Val Val Pro Ile Asp Gly Ser His Trp Leu Ser Met Arg Glu Val Leu
        35                  40                  45

Arg Glu Leu His Ala Arg Gly His Gln Ala Val Val Leu Thr Pro Glu
    50                  55                  60

Val Asn Met His Ile Lys Glu Glu Asn Phe Phe Thr Leu Thr Thr Tyr
65                  70                  75                  80

Ala Ile Ser Trp Thr Gln Asp Glu Phe Asp Arg His Val Leu Gly His
                85                  90                  95

Thr Gln Leu Tyr Phe Glu Thr Glu His Phe Leu Lys Lys Phe Phe Arg
            100                 105                 110

Ser Met Ala Met Leu Asn Asn Met Ser Leu Val Tyr His Arg Ser Cys
        115                 120                 125

Val Glu Leu Leu His Asn Glu Ala Leu Ile Arg His Leu Asn Ala Thr
    130                 135                 140

Ser Phe Asp Val Val Leu Thr Asp Pro Val Asn Leu Cys Ala Ala Val
145                 150                 155                 160

Leu Ala Lys Tyr Leu Ser Ile Pro Thr Val Phe Phe Leu Arg Asn Ile
                165                 170                 175

Pro Cys Asp Leu Asp Phe Lys Gly Thr Gln Cys Pro Asn Pro Ser Ser
            180                 185                 190

Tyr Ile Pro Arg Leu Leu Thr Thr Asn Ser Asp His Met Thr Phe Met
        195                 200                 205

Gln Arg Val Lys Asn Met Leu Tyr Pro Leu Ala Leu Ser Tyr Ile Cys
    210                 215                 220

His Ala Phe Ser Ala Pro Tyr Ala Ser Leu Ala Ser Glu Leu Phe Gln
225                 230                 235                 240

Arg Glu Val Ser Val Asp Ile Leu Ser His Ala Ser Val Trp Leu
                245                 250                 255

Phe Arg Gly Asp Phe Val Met Asp Tyr Pro Arg Pro Ile Met Pro Asn
            260                 265                 270

Met Val Phe Ile Gly Gly Ile Asn Cys Ala Asn Arg Lys Pro Leu Ser
        275                 280                 285

Gln
```

<210> SEQ ID NO 5
<211> LENGTH: 867
<212> TYPE: DNA
<213> ORGANISM: Homo sapiens
<220> FEATURE:

<221> NAME/KEY: CDS
<222> LOCATION: (1)...(867)

<400> SEQUENCE: 5

```
atg gcc aga gga ctc cag gtt ccc ctg ccg cgg ctg gcc aca gga ctg      48
Met Ala Arg Gly Leu Gln Val Pro Leu Pro Arg Leu Ala Thr Gly Leu
 1               5                  10                  15 ctg ctc ctc ctc agt gtc cag ccc tgg gct gag agt gga aag gtg ttg      96
Leu Leu Leu Leu Ser Val Gln Pro Trp Ala Glu Ser Gly Lys Val Leu
            20                  25                  30 gtg gtg ccc act gat ggc agc ccc tgg ctc agc atg cgg gag gcc ttg     144
Val Val Pro Thr Asp Gly Ser Pro Trp Leu Ser Met Arg Glu Ala Leu
         35                  40                  45 cgg gag ctc cat gcc aga ggc cac cag gcg gtg gtc ctc acc cca gag     192
Arg Glu Leu His Ala Arg Gly His Gln Ala Val Val Leu Thr Pro Glu
     50                  55                  60 gtg aat atg cac atc aaa gaa gag aaa ttt ttc acc ctg aca gcc tat     240
Val Asn Met His Ile Lys Glu Glu Lys Phe Phe Thr Leu Thr Ala Tyr
 65                  70                  75                  80 gct gtt cca tgg acc cag aag gaa ttt gat cgc gtt acg ctg ggc tac     288
Ala Val Pro Trp Thr Gln Lys Glu Phe Asp Arg Val Thr Leu Gly Tyr
                 85                  90                  95 act caa ggg ttc ttt gaa aca gaa cat ctt ctg aag aga tat tct aga     336
Thr Gln Gly Phe Phe Glu Thr Glu His Leu Leu Lys Arg Tyr Ser Arg
            100                 105                 110 agt atg gca att atg aac aat gta tct ttg gcc ctt cat agg tgt tgt     384
Ser Met Ala Ile Met Asn Asn Val Ser Leu Ala Leu His Arg Cys Cys
        115                 120                 125 gtg gag cta ctg cat aat gag gcc ctg atc agg cac ctg aat gct act     432
Val Glu Leu Leu His Asn Glu Ala Leu Ile Arg His Leu Asn Ala Thr
    130                 135                 140 tcc ttt gat gtg gtt tta aca gac ccc gtt aac ctc tgt ggg gcg gtg     480
Ser Phe Asp Val Val Leu Thr Asp Pro Val Asn Leu Cys Gly Ala Val
145                 150                 155                 160 ctg gct aag tac ctg tcg att cct gct gtg ttt ttt tgg agg tac att     528
Leu Ala Lys Tyr Leu Ser Ile Pro Ala Val Phe Phe Trp Arg Tyr Ile
                165                 170                 175 cca tgt gac tta gac ttt aag ggc aca cag tgt cca aat cct tcc tcc     576
Pro Cys Asp Leu Asp Phe Lys Gly Thr Gln Cys Pro Asn Pro Ser Ser
            180                 185                 190 tat att cct aag tta cta acg acc aat tca gac cac atg aca ttc ctg     624
Tyr Ile Pro Lys Leu Leu Thr Thr Asn Ser Asp His Met Thr Phe Leu
        195                 200                 205 caa agg gtc aag aac atg ctc tac cct ctg gcc ctg tcc tac att tgc     672
Gln Arg Val Lys Asn Met Leu Tyr Pro Leu Ala Leu Ser Tyr Ile Cys
    210                 215                 220 cat act ttt tct gcc cct tat gca agt ctt gcc tct gag ctt ttt cag     720
His Thr Phe Ser Ala Pro Tyr Ala Ser Leu Ala Ser Glu Leu Phe Gln
225                 230                 235                 240 aga gag gtg tca gtg gtg gat ctt gtc agc tat gca tcc gtg tgg ctg     768
Arg Glu Val Ser Val Val Asp Leu Val Ser Tyr Ala Ser Val Trp Leu
                245                 250                 255 ttc cga ggg gac ttt gtg atg gac tac ccc agg ccg atc atg ccc aac     816
Phe Arg Gly Asp Phe Val Met Asp Tyr Pro Arg Pro Ile Met Pro Asn
            260                 265                 270 atg gtc ttc att ggg ggc atc aac tgt gcc aac ggg aag cca cta tct     864
Met Val Phe Ile Gly Gly Ile Asn Cys Ala Asn Gly Lys Pro Leu Ser
        275                 280                 285 cag                                                                  867
Gln
```

<210> SEQ ID NO 6
<211> LENGTH: 289
<212> TYPE: PRT
<213> ORGANISM: Homo sapiens

<400> SEQUENCE: 6

```
Met Ala Arg Gly Leu Gln Val Pro Leu Pro Arg Leu Ala Thr Gly Leu
 1               5                  10                  15

Leu Leu Leu Leu Ser Val Gln Pro Trp Ala Glu Ser Gly Lys Val Leu
            20                  25                  30

Val Val Pro Thr Asp Gly Ser Pro Trp Leu Ser Met Arg Glu Ala Leu
        35                  40                  45

Arg Glu Leu His Ala Arg Gly His Gln Ala Val Val Leu Thr Pro Glu
50                  55                  60

Val Asn Met His Ile Lys Glu Lys Phe Phe Thr Leu Thr Ala Tyr
65                  70                  75                  80

Ala Val Pro Trp Thr Gln Lys Glu Phe Asp Arg Val Thr Leu Gly Tyr
                85                  90                  95

Thr Gln Gly Phe Phe Glu Thr Glu His Leu Leu Lys Arg Tyr Ser Arg
            100                 105                 110

Ser Met Ala Ile Met Asn Asn Val Ser Leu Ala Leu His Arg Cys Cys
        115                 120                 125

Val Glu Leu Leu His Asn Glu Ala Leu Ile Arg His Leu Asn Ala Thr
130                 135                 140

Ser Phe Asp Val Val Leu Thr Asp Pro Val Asn Leu Cys Gly Ala Val
145                 150                 155                 160

Leu Ala Lys Tyr Leu Ser Ile Pro Ala Val Phe Phe Trp Arg Tyr Ile
                165                 170                 175

Pro Cys Asp Leu Asp Phe Lys Gly Thr Gln Cys Pro Asn Pro Ser Ser
            180                 185                 190

Tyr Ile Pro Lys Leu Leu Thr Thr Asn Ser Asp His Met Thr Phe Leu
        195                 200                 205

Gln Arg Val Lys Asn Met Leu Tyr Pro Leu Ala Leu Ser Tyr Ile Cys
210                 215                 220

His Thr Phe Ser Ala Pro Tyr Ala Ser Leu Ala Ser Glu Leu Phe Gln
225                 230                 235                 240

Arg Glu Val Ser Val Val Asp Leu Val Ser Tyr Ala Ser Val Trp Leu
                245                 250                 255

Phe Arg Gly Asp Phe Val Met Asp Tyr Pro Arg Pro Ile Met Pro Asn
            260                 265                 270

Met Val Phe Ile Gly Gly Ile Asn Cys Ala Asn Gly Lys Pro Leu Ser
        275                 280                 285

Gln
```

<210> SEQ ID NO 7
<211> LENGTH: 867
<212> TYPE: DNA
<213> ORGANISM: Homo sapiens
<220> FEATURE:
<221> NAME/KEY: CDS
<222> LOCATION: (1)...(867)

<400> SEQUENCE: 7

```
atg gcc aca gga ctc cag gtt ccc ctg ccg cag ctg gcc aca gga ctg      48
Met Ala Thr Gly Leu Gln Val Pro Leu Pro Gln Leu Ala Thr Gly Leu
 1               5                  10                  15
```

-continued

```
ctg ctt ctc ctc agt gtc cag ccc tgg gct gag agt ggg aag gtg ctg      96
Leu Leu Leu Leu Ser Val Gln Pro Trp Ala Glu Ser Gly Lys Val Leu
             20                  25                  30 gtg gtg ccc act gat ggc agc cac tgg ctc agc atg cgg gag gcc ttg     144
Val Val Pro Thr Asp Gly Ser His Trp Leu Ser Met Arg Glu Ala Leu
         35                  40                  45 cgg gac ctc cat gcg aga ggc cac cag gtg gtg gtc ctc acc ctg gag     192
Arg Asp Leu His Ala Arg Gly His Gln Val Val Val Leu Thr Leu Glu
     50                  55                  60 gtg aat atg tac atc aaa gaa gag aac ttt ttc acc ctg aca acg tat     240
Val Asn Met Tyr Ile Lys Glu Glu Asn Phe Phe Thr Leu Thr Thr Tyr
 65                  70                  75                  80 gcc att tca tgg acc cag gac gaa ttt gat cgc ctt ttg ctg ggt cac     288
Ala Ile Ser Trp Thr Gln Asp Glu Phe Asp Arg Leu Leu Leu Gly His
                 85                  90                  95 act caa tcg ttc ttt gaa aca gaa cat ctt ctg atg aaa ttt tct aga     336
Thr Gln Ser Phe Phe Glu Thr Glu His Leu Leu Met Lys Phe Ser Arg
            100                 105                 110 aga atg gca att atg aac aat atg tct ttg atc ata cat agg tct tgt     384
Arg Met Ala Ile Met Asn Asn Met Ser Leu Ile Ile His Arg Ser Cys
        115                 120                 125 gtg gag cta ctg cat aat gag gcc ctg atc agg cac ctg cat gct act     432
Val Glu Leu Leu His Asn Glu Ala Leu Ile Arg His Leu His Ala Thr
    130                 135                 140 tcc ttt gat gtg gtt cta aca gac ccc ttt cac ctc tgc gcg gcg gtg     480
Ser Phe Asp Val Val Leu Thr Asp Pro Phe His Leu Cys Ala Ala Val
145                 150                 155                 160 ctg gct aag tac ctg tcg att cct gct gtg ttt ttc ttg agg aac att     528
Leu Ala Lys Tyr Leu Ser Ile Pro Ala Val Phe Phe Leu Arg Asn Ile
                165                 170                 175 cca tgt gat tta gac ttt aag ggc aca cag tgt cca aac cct tcc tcc     576
Pro Cys Asp Leu Asp Phe Lys Gly Thr Gln Cys Pro Asn Pro Ser Ser
            180                 185                 190 tat att cct aga tta cta acg acc aat tca gac cac atg aca ttc ctg     624
Tyr Ile Pro Arg Leu Leu Thr Thr Asn Ser Asp His Met Thr Phe Leu
        195                 200                 205 caa agg gtc aag aac atg ctc tac cct ctg gcc ctg tcc tac ctt tgc     672
Gln Arg Val Lys Asn Met Leu Tyr Pro Leu Ala Leu Ser Tyr Leu Cys
    210                 215                 220 cat gct gtt tct gct cct tat gca agc ctt gcc tct gag ctt ttt cag     720
His Ala Val Ser Ala Pro Tyr Ala Ser Leu Ala Ser Glu Leu Phe Gln
225                 230                 235                 240 aga gag gtg tca gtg gtg gat ctt gtc agc cat gca tct gtg tgg ctg     768
Arg Glu Val Ser Val Val Asp Leu Val Ser His Ala Ser Val Trp Leu
                245                 250                 255 ttc cga ggg gac ttt gtg atg gat tac ccc agg ccg atc atg ccc aac     816
Phe Arg Gly Asp Phe Val Met Asp Tyr Pro Arg Pro Ile Met Pro Asn
            260                 265                 270 atg gtc ttc att ggg ggc atc aac tgt gcc aac ggg aag cca cta tct     864
Met Val Phe Ile Gly Gly Ile Asn Cys Ala Asn Gly Lys Pro Leu Ser
        275                 280                 285 cag                                                                 867
Gln
```

<210> SEQ ID NO 8
<211> LENGTH: 289
<212> TYPE: PRT
<213> ORGANISM: Homo sapiens

<400> SEQUENCE: 8

```
Met Ala Thr Gly Leu Gln Val Pro Leu Pro Gln Leu Ala Thr Gly Leu
 1               5                  10                  15
Leu Leu Leu Leu Ser Val Gln Pro Trp Ala Glu Ser Gly Lys Val Leu
            20                  25                  30
Val Val Pro Thr Asp Gly Ser His Trp Leu Ser Met Arg Glu Ala Leu
        35                  40                  45
Arg Asp Leu His Ala Arg Gly His Gln Val Val Leu Thr Leu Glu
    50                  55                  60
Val Asn Met Tyr Ile Lys Glu Glu Asn Phe Phe Thr Leu Thr Thr Tyr
 65                  70                  75                  80
Ala Ile Ser Trp Thr Gln Asp Glu Phe Asp Arg Leu Leu Leu Gly His
                85                  90                  95
Thr Gln Ser Phe Phe Glu Thr Glu His Leu Leu Met Lys Phe Ser Arg
            100                 105                 110
Arg Met Ala Ile Met Asn Asn Met Ser Leu Ile Ile His Arg Ser Cys
        115                 120                 125
Val Glu Leu Leu His Asn Glu Ala Leu Ile Arg His Leu His Ala Thr
    130                 135                 140
Ser Phe Asp Val Val Leu Thr Asp Pro Phe His Leu Cys Ala Ala Val
145                 150                 155                 160
Leu Ala Lys Tyr Leu Ser Ile Pro Ala Val Phe Phe Leu Arg Asn Ile
                165                 170                 175
Pro Cys Asp Leu Asp Phe Lys Gly Thr Gln Cys Pro Asn Pro Ser Ser
            180                 185                 190
Tyr Ile Pro Arg Leu Leu Thr Thr Asn Ser Asp His Met Thr Phe Leu
        195                 200                 205
Gln Arg Val Lys Asn Met Leu Tyr Pro Leu Ala Leu Ser Tyr Leu Cys
    210                 215                 220
His Ala Val Ser Ala Pro Tyr Ala Ser Leu Ala Ser Glu Leu Phe Gln
225                 230                 235                 240
Arg Glu Val Ser Val Val Asp Leu Val Ser His Ala Ser Val Trp Leu
                245                 250                 255
Phe Arg Gly Asp Phe Val Met Asp Tyr Pro Arg Pro Ile Met Pro Asn
            260                 265                 270
Met Val Phe Ile Gly Gly Ile Asn Cys Ala Asn Gly Lys Pro Leu Ser
        275                 280                 285
Gln
```

<210> SEQ ID NO 9
<211> LENGTH: 861
<212> TYPE: DNA
<213> ORGANISM: Homo sapiens
<220> FEATURE:
<221> NAME/KEY: CDS
<222> LOCATION: (1)...(861)

<400> SEQUENCE: 9

```
atg gcc tgc ctc ctt cgc tca ttt cag aga att tct gca ggg gtt ttc    48
Met Ala Cys Leu Leu Arg Ser Phe Gln Arg Ile Ser Ala Gly Val Phe
 1               5                  10                  15 ttc tta gca ctt tgg ggc atg gtt gta ggt gac aag ctg ctg gtg gtc    96
Phe Leu Ala Leu Trp Gly Met Val Val Gly Asp Lys Leu Leu Val Val
            20                  25                  30 cct cag gac gga agc cac tgg ctt agt atg aag gat ata gtt gag gtt   144
Pro Gln Asp Gly Ser His Trp Leu Ser Met Lys Asp Ile Val Glu Val
        35                  40                  45
```

```
ctc agt gac cgg ggt cat gag att gta gtg gtg gtg cct gaa gtt aat     192
Leu Ser Asp Arg Gly His Glu Ile Val Val Val Val Pro Glu Val Asn
     50                  55                  60 ttg ctt ttg aaa gaa tcc aaa tac tac aca aga aaa atc tat cca gtg     240
Leu Leu Leu Lys Glu Ser Lys Tyr Tyr Thr Arg Lys Ile Tyr Pro Val
 65                  70                  75                  80 ccg tat gac caa gaa gag ctg aag aac cgt tac caa tca ttt gga aac     288
Pro Tyr Asp Gln Glu Glu Leu Lys Asn Arg Tyr Gln Ser Phe Gly Asn
                 85                  90                  95 aat cac ttt gct gag cga tca ttc cta act gct cct cag aca gag tac     336
Asn His Phe Ala Glu Arg Ser Phe Leu Thr Ala Pro Gln Thr Glu Tyr
            100                 105                 110 agg aat aac atg att gtt att ggc ctg tac ttc atc aac tgc cag agc     384
Arg Asn Asn Met Ile Val Ile Gly Leu Tyr Phe Ile Asn Cys Gln Ser
        115                 120                 125 ctc ctg cag gac agg gac acc ctg aac ttc ttt aag gag agc aag ttt     432
Leu Leu Gln Asp Arg Asp Thr Leu Asn Phe Phe Lys Glu Ser Lys Phe
    130                 135                 140 gat gct ctt ttc aca gac cca gcc tta ccc tgt ggg gtg atc ctg gct     480
Asp Ala Leu Phe Thr Asp Pro Ala Leu Pro Cys Gly Val Ile Leu Ala
145                 150                 155                 160 gag tat ttg ggc cta cca tct gtg tac ctc ttc agg ggt ttt ccg tgt     528
Glu Tyr Leu Gly Leu Pro Ser Val Tyr Leu Phe Arg Gly Phe Pro Cys
                165                 170                 175 tcc ctg gag cat aca ttc agc aga agc cca gac cct gtg tcc tac att     576
Ser Leu Glu His Thr Phe Ser Arg Ser Pro Asp Pro Val Ser Tyr Ile
            180                 185                 190 ccc agg tgc tac aca aag ttt tca gac cac atg act ttt tcc caa cga     624
Pro Arg Cys Tyr Thr Lys Phe Ser Asp His Met Thr Phe Ser Gln Arg
        195                 200                 205 gtg gcc aac ttc ctt gtt aat ttg ttg gag ccc tat cta ttt tat tgt     672
Val Ala Asn Phe Leu Val Asn Leu Leu Glu Pro Tyr Leu Phe Tyr Cys
    210                 215                 220 ctg ttt tca aag tat gaa gaa ctc gca tca gct gtc ctc aag aga gat     720
Leu Phe Ser Lys Tyr Glu Glu Leu Ala Ser Ala Val Leu Lys Arg Asp
225                 230                 235                 240 gtg gat ata atc acc tta tat cag aag gtc tct gtt tgg ctg tta aga     768
Val Asp Ile Ile Thr Leu Tyr Gln Lys Val Ser Val Trp Leu Leu Arg
                245                 250                 255 tat gac ttt gtg ctt gaa tat cct agg ccg gtc atg ccc aac atg gtc     816
Tyr Asp Phe Val Leu Glu Tyr Pro Arg Pro Val Met Pro Asn Met Val
            260                 265                 270 ttc att gga ggt atc aac tgt aag aag agg aaa gac ttg tct cag         861
Phe Ile Gly Gly Ile Asn Cys Lys Lys Arg Lys Asp Leu Ser Gln
        275                 280                 285

<210> SEQ ID NO 10
<211> LENGTH: 287
<212> TYPE: PRT
<213> ORGANISM: Homo sapiens

<400> SEQUENCE: 10

Met Ala Cys Leu Leu Arg Ser Phe Gln Arg Ile Ser Ala Gly Val Phe
  1               5                  10                  15

Phe Leu Ala Leu Trp Gly Met Val Val Gly Asp Lys Leu Leu Val
                 20                  25                  30

Pro Gln Asp Gly Ser His Trp Leu Ser Met Lys Asp Ile Val Glu Val
             35                  40                  45

Leu Ser Asp Arg Gly His Glu Ile Val Val Val Val Pro Glu Val Asn
```

```
                    50                  55                  60
Leu Leu Leu Lys Glu Ser Lys Tyr Tyr Thr Arg Lys Ile Tyr Pro Val
 65                  70                  75                  80

Pro Tyr Asp Gln Glu Leu Lys Asn Arg Tyr Gln Ser Phe Gly Asn
                 85                  90                  95

Asn His Phe Ala Glu Arg Ser Phe Leu Thr Ala Pro Gln Thr Glu Tyr
                100                 105                 110

Arg Asn Asn Met Ile Val Ile Gly Leu Tyr Phe Ile Asn Cys Gln Ser
                115                 120                 125

Leu Leu Gln Asp Arg Asp Thr Leu Asn Phe Phe Lys Glu Ser Lys Phe
            130                 135                 140

Asp Ala Leu Phe Thr Asp Pro Ala Leu Pro Cys Gly Val Ile Leu Ala
145                 150                 155                 160

Glu Tyr Leu Gly Leu Pro Ser Val Tyr Leu Phe Arg Gly Phe Pro Cys
                165                 170                 175

Ser Leu Glu His Thr Phe Ser Arg Ser Pro Asp Pro Val Ser Tyr Ile
                180                 185                 190

Pro Arg Cys Tyr Thr Lys Phe Ser Asp His Met Thr Phe Ser Gln Arg
                195                 200                 205

Val Ala Asn Phe Leu Val Asn Leu Leu Glu Pro Tyr Leu Phe Tyr Cys
            210                 215                 220

Leu Phe Ser Lys Tyr Glu Glu Leu Ala Ser Ala Val Leu Lys Arg Asp
225                 230                 235                 240

Val Asp Ile Ile Thr Leu Tyr Gln Lys Val Ser Val Trp Leu Leu Arg
                245                 250                 255

Tyr Asp Phe Val Leu Glu Tyr Pro Arg Pro Val Met Pro Asn Met Val
            260                 265                 270

Phe Ile Gly Gly Ile Asn Cys Lys Lys Arg Lys Asp Leu Ser Gln
            275                 280                 285

<210> SEQ ID NO 11
<211> LENGTH: 1115
<212> TYPE: DNA
<213> ORGANISM: Homo sapiens
<220> FEATURE:
<221> NAME/KEY: CDS
<222> LOCATION: (165)...(1115)

<400> SEQUENCE: 11 tgta ttattatgag taaatcattg gcagtgaatg tgaattttt        44 tttaaatgaa tgaataagta cacgccttct tttgagggca ggttctatct gtacttcttc     104
cacttactat attataggag cttagaatcc cagctgctgg ctctgggctg aagttctctg     164 atg gct cgt gca ggg tgg act ggc ctc ctt ccc cta tat gtg tgt cta      212
Met Ala Arg Ala Gly Trp Thr Gly Leu Leu Pro Leu Tyr Val Cys Leu
 1               5                  10                  15 ctg ctg acc tgt gct ttg cca agg tca ggg aag ctg ctg gta gtg ccc      260
Leu Leu Thr Cys Ala Leu Pro Arg Ser Gly Lys Leu Leu Val Val Pro
                20                  25                  30 atg gat ggg agc cac tgg ttc acc atg cag tcg gtg gtg gag aaa ctc      308
Met Asp Gly Ser His Trp Phe Thr Met Gln Ser Val Val Glu Lys Leu
            35                  40                  45 atc ctc agg ggg cat gag gtg gtc gta gtc atg cca gag gtg agt tgg      356
Ile Leu Arg Gly His Glu Val Val Val Val Met Pro Glu Val Ser Trp
 50                  55                  60 caa ctg gga aga tca ctg aat tgc aca gtg aag act tac tca acc tca      404
Gln Leu Gly Arg Ser Leu Asn Cys Thr Val Lys Thr Tyr Ser Thr Ser
```

-continued

```
                    65                  70                  75                  80
tac act ctg gag gat cag gac cgg gag ttc atg gtt ttt gcc gat gct       452
Tyr Thr Leu Glu Asp Gln Asp Arg Glu Phe Met Val Phe Ala Asp Ala
                    85                  90                  95 cgc tgg acg gca cca ttg cga agt gca ttt tct cta tta aca agt tca       500
Arg Trp Thr Ala Pro Leu Arg Ser Ala Phe Ser Leu Leu Thr Ser Ser
                100                 105                 110 tcc aat ggt att ttt gac tta ttt ttt tca aat tgc agg agt ttg ttt       548
Ser Asn Gly Ile Phe Asp Leu Phe Phe Ser Asn Cys Arg Ser Leu Phe
            115                 120                 125 aat gac cga aaa tta gta gaa tac tta aag gag agt tgt ttt gat gca       596
Asn Asp Arg Lys Leu Val Glu Tyr Leu Lys Glu Ser Cys Phe Asp Ala
        130                 135                 140 gtg ttt ctc gat cct ttt gat cgc tgt ggc tta att gtt gcc aaa tat       644
Val Phe Leu Asp Pro Phe Asp Arg Cys Gly Leu Ile Val Ala Lys Tyr
145                 150                 155                 160 ttc tcc ctc ccc tct gtg gtc ttc gcc agg gga ata ttt tgc cac tat       692
Phe Ser Leu Pro Ser Val Val Phe Ala Arg Gly Ile Phe Cys His Tyr
                165                 170                 175 ctt gaa gaa ggt gca cag tgc cct gct cct ctt tcc tat gtc ccc aga       740
Leu Glu Glu Gly Ala Gln Cys Pro Ala Pro Leu Ser Tyr Val Pro Arg
            180                 185                 190 ctt ctc tta ggg ttc tca gac gcc atg act ttc aag gag aga gta tgg      788
Leu Leu Leu Gly Phe Ser Asp Ala Met Thr Phe Lys Glu Arg Val Trp
        195                 200                 205 aac cac atc atg cac ttg gag gaa cat tta ttt tgc ccc tat ttt ttc       836
Asn His Ile Met His Leu Glu Glu His Leu Phe Cys Pro Tyr Phe Phe
    210                 215                 220 aaa aat gtc tta gaa ata gcc tct gaa att ctc caa acc cct gtc acg       884
Lys Asn Val Leu Glu Ile Ala Ser Glu Ile Leu Gln Thr Pro Val Thr
225                 230                 235                 240 gca tat gat ctc tac agc cac aca tca att tgg ttg ttg cga act gac       932
Ala Tyr Asp Leu Tyr Ser His Thr Ser Ile Trp Leu Leu Arg Thr Asp
                245                 250                 255 ttt gtt ttg gag tat ccc aaa ccc gtg atg ccc aat atg atc ttc att       980
Phe Val Leu Glu Tyr Pro Lys Pro Val Met Pro Asn Met Ile Phe Ile
            260                 265                 270 ggt ggt atc aac tgt cat cag gga aag cca gtg cct atg gta agt tat      1028
Gly Gly Ile Asn Cys His Gln Gly Lys Pro Val Pro Met Val Ser Tyr
        275                 280                 285 ctc ccc ttt agc aca tta aga ata atc tgg ctt tgg aaa tta aaa gat      1076
Leu Pro Phe Ser Thr Leu Arg Ile Ile Trp Leu Trp Lys Leu Lys Asp
    290                 295                 300 ttc tta cag aat cat aat tta tca ttt aca ttt gtc cca                   1115
Phe Leu Gln Asn His Asn Leu Ser Phe Thr Phe Val Pro
305                 310                 315

<210> SEQ ID NO 12
<211> LENGTH: 317
<212> TYPE: PRT
<213> ORGANISM: Homo sapiens

<400> SEQUENCE: 12

Met Ala Arg Ala Gly Trp Thr Gly Leu Leu Pro Leu Tyr Val Cys Leu
1               5                   10                  15

Leu Leu Thr Cys Ala Leu Pro Arg Ser Gly Lys Leu Leu Val Val Pro
            20                  25                  30

Met Asp Gly Ser His Trp Phe Thr Met Gln Ser Val Val Glu Lys Leu
        35                  40                  45
```

| Ile | Leu | Arg | Gly | His | Glu | Val | Val | Val | Met | Pro | Glu | Val | Ser | Trp |
|---|---|---|---|---|---|---|---|---|---|---|---|---|---|---|
| | 50 | | | | 55 | | | | 60 | | | | | |

Gln Leu Gly Arg Ser Leu Asn Cys Thr Val Lys Thr Tyr Ser Thr Ser
65              70                 75              80

Tyr Thr Leu Glu Asp Gln Asp Arg Glu Phe Met Val Phe Ala Asp Ala
              85                90                95

Arg Trp Thr Ala Pro Leu Arg Ser Ala Phe Ser Leu Leu Thr Ser Ser
            100              105            110

Ser Asn Gly Ile Phe Asp Leu Phe Phe Ser Asn Cys Arg Ser Leu Phe
        115              120              125

Asn Asp Arg Lys Leu Val Glu Tyr Leu Lys Glu Ser Cys Phe Asp Ala
    130              135              140

Val Phe Leu Asp Pro Phe Asp Arg Cys Gly Leu Ile Val Ala Lys Tyr
145              150              155            160

Phe Ser Leu Pro Ser Val Val Phe Ala Arg Gly Ile Phe Cys His Tyr
            165              170            175

Leu Glu Glu Gly Ala Gln Cys Pro Ala Pro Leu Ser Tyr Val Pro Arg
        180              185              190

Leu Leu Leu Gly Phe Ser Asp Ala Met Thr Phe Lys Glu Arg Val Trp
    195              200              205

Asn His Ile Met His Leu Glu Glu His Leu Phe Cys Pro Tyr Phe Phe
    210              215              220

Lys Asn Val Leu Glu Ile Ala Ser Glu Ile Leu Gln Thr Pro Val Thr
225              230              235            240

Ala Tyr Asp Leu Tyr Ser His Thr Ser Ile Trp Leu Leu Arg Thr Asp
            245              250            255

Phe Val Leu Glu Tyr Pro Lys Pro Val Met Pro Asn Met Ile Phe Ile
        260              265              270

Gly Gly Ile Asn Cys His Gln Gly Lys Pro Val Pro Met Val Ser Tyr
        275              280            285

Leu Pro Phe Ser Thr Leu Arg Ile Ile Trp Leu Trp Lys Leu Lys Asp
    290              295              300

Phe Leu Gln Asn His Asn Leu Ser Phe Thr Phe Val Pro
305              310              315

<210> SEQ ID NO 13
<211> LENGTH: 930
<212> TYPE: DNA
<213> ORGANISM: Homo sapiens
<220> FEATURE:
<221> NAME/KEY: CDS
<222> LOCATION: (1)...(930)

<400> SEQUENCE: 13

```
atg gct cgc aca ggg tgg acc agc ccc att ccc cta tgt gtt tct ctg      48
Met Ala Arg Thr Gly Trp Thr Ser Pro Ile Pro Leu Cys Val Ser Leu
 1               5                  10                  15 ctg ctg acc tgt ggc ttt gct gag gca ggg aag ctg ctg gta gtg ccc      96
Leu Leu Thr Cys Gly Phe Ala Glu Ala Gly Lys Leu Leu Val Val Pro
             20                  25                  30 atg gat ggg agt cac tgg ttc acc atg cag tcg gtg gtg gag aaa ctt     144
Met Asp Gly Ser His Trp Phe Thr Met Gln Ser Val Val Glu Lys Leu
         35                  40                  45 atc ctc agg ggg cat gag gtg gtt gta gtc atg cca gag gtg agt tgg     192
Ile Leu Arg Gly His Glu Val Val Val Val Met Pro Glu Val Ser Trp
     50                  55                  60 caa ctg gga aaa tca ctg aat tgc aca gtg aag act tac tca acc tca     240
```

```
Gln Leu Gly Lys Ser Leu Asn Cys Thr Val Lys Thr Tyr Ser Thr Ser
 65                  70                  75                  80 tac act ctg gag gat ctg gac cgg gaa ttc atg gat ttc gcc gat gct    288
Tyr Thr Leu Glu Asp Leu Asp Arg Glu Phe Met Asp Phe Ala Asp Ala
                 85                  90                  95 caa tgg aaa gca caa gta cga agt ttg ttt tct cta ttt ctg agt tca    336
Gln Trp Lys Ala Gln Val Arg Ser Leu Phe Ser Leu Phe Leu Ser Ser
            100                 105                 110 tcc aat ggt ttt ttt aac tta ttt ttt tcg cat tgc agg agt ttg ttt    384
Ser Asn Gly Phe Phe Asn Leu Phe Phe Ser His Cys Arg Ser Leu Phe
        115                 120                 125 aat gac cga aaa tta gta gaa tac tta aag gag agt tct ttt gat gcg    432
Asn Asp Arg Lys Leu Val Glu Tyr Leu Lys Glu Ser Ser Phe Asp Ala
    130                 135                 140 gtg ttt ctt gat cct ttt gat gcc tgt gcg tta att gtt gcc aaa tat    480
Val Phe Leu Asp Pro Phe Asp Ala Cys Ala Leu Ile Val Ala Lys Tyr
145                 150                 155                 160 ttc tcc ctc ccc tct gtg gtc ttc gcc agg gga ata ggt tgc cac tat    528
Phe Ser Leu Pro Ser Val Val Phe Ala Arg Gly Ile Gly Cys His Tyr
                165                 170                 175 ctt gaa gaa ggt gca cag tgc cct gct cct ctt tcc tat gtc ccc aga    576
Leu Glu Glu Gly Ala Gln Cys Pro Ala Pro Leu Ser Tyr Val Pro Arg
            180                 185                 190 att ctc tta ggg ttc tca gat gcc atg act ttc aag gag aga gta cgg    624
Ile Leu Leu Gly Phe Ser Asp Ala Met Thr Phe Lys Glu Arg Val Arg
        195                 200                 205 aac cac atc atg cac ttg gag gaa cat tta ttt tgc cag tat ttt tcc    672
Asn His Ile Met His Leu Glu Glu His Leu Phe Cys Gln Tyr Phe Ser
    210                 215                 220 aaa aat gcc cta gaa ata gcc tct gaa att ctc caa aca cct gtc aca    720
Lys Asn Ala Leu Glu Ile Ala Ser Glu Ile Leu Gln Thr Pro Val Thr
225                 230                 235                 240 gca tat gat ctc tac agc cac aca tca att tgg ttg ttg cga aca gac    768
Ala Tyr Asp Leu Tyr Ser His Thr Ser Ile Trp Leu Leu Arg Thr Asp
                245                 250                 255 ttt gtt ttg gac tat ccc aaa ccc gtg atg ccc aat atg atc ttc att    816
Phe Val Leu Asp Tyr Pro Lys Pro Val Met Pro Asn Met Ile Phe Ile
            260                 265                 270 ggt ggt atc aac tgc cat cag gga aag cca ttg cct atg gta agt cac    864
Gly Gly Ile Asn Cys His Gln Gly Lys Pro Leu Pro Met Val Ser His
        275                 280                 285 ctc tcc ttt agc aca tta gga ata atc ttg gct ttg gaa att aaa aaa    912
Leu Ser Phe Ser Thr Leu Gly Ile Ile Leu Ala Leu Glu Ile Lys Lys
    290                 295                 300 aga ttc ctt act gaa ttg                                            930
Arg Phe Leu Thr Glu Leu
305                 310

<210> SEQ ID NO 14
<211> LENGTH: 310
<212> TYPE: PRT
<213> ORGANISM: Homo sapiens

<400> SEQUENCE: 14

Met Ala Arg Thr Gly Trp Thr Ser Pro Ile Pro Leu Cys Val Ser Leu
 1               5                  10                  15

Leu Leu Thr Cys Gly Phe Ala Glu Ala Gly Lys Leu Leu Val Val Pro
                20                  25                  30

Met Asp Gly Ser His Trp Phe Thr Met Gln Ser Val Val Glu Lys Leu
            35                  40                  45
```

-continued

```
Ile Leu Arg Gly His Glu Val Val Val Met Pro Glu Val Ser Trp
        50                  55                  60
Gln Leu Gly Lys Ser Leu Asn Cys Thr Val Lys Thr Tyr Ser Thr Ser
 65                  70                  75                  80
Tyr Thr Leu Glu Asp Leu Asp Arg Glu Phe Met Asp Phe Ala Asp Ala
                 85                  90                  95
Gln Trp Lys Ala Gln Val Arg Ser Leu Phe Ser Leu Phe Leu Ser Ser
                100                 105                 110
Ser Asn Gly Phe Phe Asn Leu Phe Ser His Cys Arg Ser Leu Phe
            115                 120                 125
Asn Asp Arg Lys Leu Val Glu Tyr Leu Lys Glu Ser Ser Phe Asp Ala
130                 135                 140
Val Phe Leu Asp Pro Phe Asp Ala Cys Ala Leu Ile Val Ala Lys Tyr
145                 150                 155                 160
Phe Ser Leu Pro Ser Val Val Phe Ala Arg Gly Ile Gly Cys His Tyr
                165                 170                 175
Leu Glu Glu Gly Ala Gln Cys Pro Ala Pro Leu Ser Tyr Val Pro Arg
                180                 185                 190
Ile Leu Leu Gly Phe Ser Asp Ala Met Thr Phe Lys Glu Arg Val Arg
                195                 200                 205
Asn His Ile Met His Leu Glu Glu His Leu Phe Cys Gln Tyr Phe Ser
210                 215                 220
Lys Asn Ala Leu Glu Ile Ala Ser Glu Ile Leu Gln Thr Pro Val Thr
225                 230                 235                 240
Ala Tyr Asp Leu Tyr Ser His Thr Ser Ile Trp Leu Leu Arg Thr Asp
                245                 250                 255
Phe Val Leu Asp Tyr Pro Lys Pro Val Met Pro Asn Met Ile Phe Ile
                260                 265                 270
Gly Gly Ile Asn Cys His Gln Gly Lys Pro Leu Pro Met Val Ser His
                275                 280                 285
Leu Ser Phe Ser Thr Leu Gly Ile Ile Leu Ala Leu Glu Ile Lys Lys
            290                 295                 300
Arg Phe Leu Thr Glu Leu
305                 310

<210> SEQ ID NO 15
<211> LENGTH: 759
<212> TYPE: DNA
<213> ORGANISM: Homo sapiens
<220> FEATURE:
<221> NAME/KEY: CDS
<222> LOCATION: (1)...(759)

<400> SEQUENCE: 15 atg gat ggg agt cac tgg ttc acc atg cag tcg gtg gtg gag aaa ctt     48
Met Asp Gly Ser His Trp Phe Thr Met Gln Ser Val Val Glu Lys Leu
 1               5                  10                  15 atc ctc agg ggg cat gag gtg gtt gta gtc atg cca gag gtg agt tgg     96
Ile Leu Arg Gly His Glu Val Val Val Val Met Pro Glu Val Ser Trp
            20                  25                  30 caa ctg gaa aga tca ctg aat tgc aca gtg aag act tac tca acc tcg    144
Gln Leu Glu Arg Ser Leu Asn Cys Thr Val Lys Thr Tyr Ser Thr Ser
        35                  40                  45 tac act ctg gaa gat cag aac cgg gaa ttc atg gtt ttc gcc cat gct    192
Tyr Thr Leu Glu Asp Gln Asn Arg Glu Phe Met Val Phe Ala His Ala
    50                  55                  60
```

```
caa tgg aaa gca cag gca caa agt ata ttt tct cta tta atg agt tca      240
Gln Trp Lys Ala Gln Ala Gln Ser Ile Phe Ser Leu Leu Met Ser Ser
 65                  70                  75                  80 tcc agt ggt ttt ctt gac tta ttt ttt tcg cat tgc agg agt ttg ttt      288
Ser Ser Gly Phe Leu Asp Leu Phe Phe Ser His Cys Arg Ser Leu Phe
                     85                  90                  95 aat gac cga aaa tta gta gaa tac tta aag gag agt tct ttt gat gca      336
Asn Asp Arg Lys Leu Val Glu Tyr Leu Lys Glu Ser Ser Phe Asp Ala
                100                 105                 110 gtg ttt ctg gat cct ttt gat acc tgt ggc tta att gtt gct aaa tat      384
Val Phe Leu Asp Pro Phe Asp Thr Cys Gly Leu Ile Val Ala Lys Tyr
            115                 120                 125 ttc tcc ctc ccc tct gtg gtc ttc acc agg gga ata ttt tgc cac cat      432
Phe Ser Leu Pro Ser Val Val Phe Thr Arg Gly Ile Phe Cys His His
        130                 135                 140 ctt gaa gaa ggt gca cag tgc cct gct cct ctt tcc tat gtc ccc aat      480
Leu Glu Glu Gly Ala Gln Cys Pro Ala Pro Leu Ser Tyr Val Pro Asn
145                 150                 155                 160 gat ctc tta ggg ttc tca gat gcc atg act ttc aag gag aga gta tgg      528
Asp Leu Leu Gly Phe Ser Asp Ala Met Thr Phe Lys Glu Arg Val Trp
                165                 170                 175 aac cac atc gtg cac ttg gag gac cat tta ttt tgc cag tat ctt ttt      576
Asn His Ile Val His Leu Glu Asp His Leu Phe Cys Gln Tyr Leu Phe
                180                 185                 190 aga aat gcc cta gaa ata gcc tct gaa att ctc caa acc cct gtc acg      624
Arg Asn Ala Leu Glu Ile Ala Ser Glu Ile Leu Gln Thr Pro Val Thr
            195                 200                 205 gca tat gat ctc tac agt cac aca tca att tgg ttg ttg cga acg gac      672
Ala Tyr Asp Leu Tyr Ser His Thr Ser Ile Trp Leu Leu Arg Thr Asp
        210                 215                 220 ttt gtt ttg gac tat ccc aaa ccc gtg atg ccc aac atg atc ttc att      720
Phe Val Leu Asp Tyr Pro Lys Pro Val Met Pro Asn Met Ile Phe Ile
225                 230                 235                 240 ggt ggt atc aac tgt cat cag gga aag cca ttg cct atg                  759
Gly Gly Ile Asn Cys His Gln Gly Lys Pro Leu Pro Met
                245                 250

<210> SEQ ID NO 16
<211> LENGTH: 253
<212> TYPE: PRT
<213> ORGANISM: Homo sapiens

<400> SEQUENCE: 16

Met Asp Gly Ser His Trp Phe Thr Met Gln Ser Val Val Glu Lys Leu
 1               5                  10                  15

Ile Leu Arg Gly His Glu Val Val Val Met Pro Glu Val Ser Trp
             20                  25                  30

Gln Leu Glu Arg Ser Leu Asn Cys Thr Val Lys Thr Tyr Ser Thr Ser
         35                  40                  45

Tyr Thr Leu Glu Asp Gln Asn Arg Glu Phe Met Val Phe Ala His Ala
     50                  55                  60

Gln Trp Lys Ala Gln Ala Gln Ser Ile Phe Ser Leu Leu Met Ser Ser
 65                  70                  75                  80

Ser Ser Gly Phe Leu Asp Leu Phe Phe Ser His Cys Arg Ser Leu Phe
                 85                  90                  95

Asn Asp Arg Lys Leu Val Glu Tyr Leu Lys Glu Ser Ser Phe Asp Ala
            100                 105                 110

Val Phe Leu Asp Pro Phe Asp Thr Cys Gly Leu Ile Val Ala Lys Tyr
        115                 120                 125
```

```
Phe Ser Leu Pro Ser Val Val Phe Thr Arg Gly Ile Phe Cys His His
    130                 135                 140

Leu Glu Glu Gly Ala Gln Cys Pro Ala Pro Leu Ser Tyr Val Pro Asn
145                 150                 155                 160

Asp Leu Leu Gly Phe Ser Asp Ala Met Thr Phe Lys Glu Arg Val Trp
                165                 170                 175

Asn His Ile Val His Leu Glu Asp His Leu Phe Cys Gln Tyr Leu Phe
            180                 185                 190

Arg Asn Ala Leu Glu Ile Ala Ser Glu Ile Leu Gln Thr Pro Val Thr
        195                 200                 205

Ala Tyr Asp Leu Tyr Ser His Thr Ser Ile Trp Leu Leu Arg Thr Asp
    210                 215                 220

Phe Val Leu Asp Tyr Pro Lys Pro Val Met Pro Asn Met Ile Phe Ile
225                 230                 235                 240

Gly Gly Ile Asn Cys His Gln Gly Lys Pro Leu Pro Met
                245                 250

<210> SEQ ID NO 17
<211> LENGTH: 735
<212> TYPE: DNA
<213> ORGANISM: Homo sapiens
<220> FEATURE:
<221> NAME/KEY: CDS
<222> LOCATION: (1)...(735)

<400> SEQUENCE: 17 gaa ttt gaa gcc tac att aat gct tct gga gaa cat gga att gtg gtt      48
Glu Phe Glu Ala Tyr Ile Asn Ala Ser Gly Glu His Gly Ile Val Val
1               5                   10                  15 ttc tct ttg gga tca atg gtc tca gaa att cca gag aag aaa gct atg     96
Phe Ser Leu Gly Ser Met Val Ser Glu Ile Pro Glu Lys Lys Ala Met
            20                  25                  30 gca att gct gat gct ttg ggc aaa atc cct cag aca gtc ctg tgg cgg    144
Ala Ile Ala Asp Ala Leu Gly Lys Ile Pro Gln Thr Val Leu Trp Arg
        35                  40                  45 tac act gga acc cga cca tcg aat ctt gcg aac aac acg ata ctt gtt    192
Tyr Thr Gly Thr Arg Pro Ser Asn Leu Ala Asn Asn Thr Ile Leu Val
    50                  55                  60 aag tgg cta ccc caa aac gat ctg ctt ggt cac ccg atg acc cgt gcc    240
Lys Trp Leu Pro Gln Asn Asp Leu Leu Gly His Pro Met Thr Arg Ala
65                  70                  75                  80 ttt atc acc cat gct ggt tcc cat ggt gtt tat gaa agc ata tgc aat    288
Phe Ile Thr His Ala Gly Ser His Gly Val Tyr Glu Ser Ile Cys Asn
                85                  90                  95 ggc gtt ccc atg gtg atg atg ccc ttg ttt ggt gat cag atg gac aat    336
Gly Val Pro Met Val Met Met Pro Leu Phe Gly Asp Gln Met Asp Asn
            100                 105                 110 gca aag cgc atg gag act aag gga gct gga gtg acc ctg aat gtt ctg    384
Ala Lys Arg Met Glu Thr Lys Gly Ala Gly Val Thr Leu Asn Val Leu
        115                 120                 125 gaa atg act tct gaa gat tta gaa aat gct cta aaa gca gtc atc aat    432
Glu Met Thr Ser Glu Asp Leu Glu Asn Ala Leu Lys Ala Val Ile Asn
    130                 135                 140 gac aaa agt tac aag gag aac atc atg cgc ctc tcc agc ctt cac aag    480
Asp Lys Ser Tyr Lys Glu Asn Ile Met Arg Leu Ser Ser Leu His Lys
145                 150                 155                 160 gac cgc ccg gtg gag ccg ctg gac ctg gcc gtg ttc tgg gtg gag ttt    528
Asp Arg Pro Val Glu Pro Leu Asp Leu Ala Val Phe Trp Val Glu Phe
                165                 170                 175
```

```
gtg atg agg cac aag ggc gcg cca cac ctg cgc ccc gca gcc cac gac      576
Val Met Arg His Lys Gly Ala Pro His Leu Arg Pro Ala Ala His Asp
            180                 185                 190 ctc acc tgg tac cag tac cat tcc ttg gac gtg att ggt ttc ctc ttg      624
Leu Thr Trp Tyr Gln Tyr His Ser Leu Asp Val Ile Gly Phe Leu Leu
        195                 200                 205 gcc gtc gtg ctg aca gtg gcc ttc atc acc ttt aaa tgt tgt gct tat      672
Ala Val Val Leu Thr Val Ala Phe Ile Thr Phe Lys Cys Cys Ala Tyr
    210                 215                 220 ggc tac cgg aaa tgc ttg ggg aaa aaa ggg cga gtt aag aaa gcc cac      720
Gly Tyr Arg Lys Cys Leu Gly Lys Lys Gly Arg Val Lys Lys Ala His
225                 230                 235                 240 aaa tcc aag acc cat                                                  735
Lys Ser Lys Thr His
                245

<210> SEQ ID NO 18
<211> LENGTH: 245
<212> TYPE: PRT
<213> ORGANISM: Homo sapiens

<400> SEQUENCE: 18

Glu Phe Glu Ala Tyr Ile Asn Ala Ser Gly Glu His Gly Ile Val Val
1               5                   10                  15

Phe Ser Leu Gly Ser Met Val Ser Glu Ile Pro Glu Lys Lys Ala Met
            20                  25                  30

Ala Ile Ala Asp Ala Leu Gly Lys Ile Pro Gln Thr Val Leu Trp Arg
        35                  40                  45

Tyr Thr Gly Thr Arg Pro Ser Asn Leu Ala Asn Asn Thr Ile Leu Val
    50                  55                  60

Lys Trp Leu Pro Gln Asn Asp Leu Leu Gly His Pro Met Thr Arg Ala
65                  70                  75                  80

Phe Ile Thr His Ala Gly Ser His Gly Val Tyr Glu Ser Ile Cys Asn
                85                  90                  95

Gly Val Pro Met Val Met Met Pro Leu Phe Gly Asp Gln Met Asp Asn
            100                 105                 110

Ala Lys Arg Met Glu Thr Lys Gly Ala Gly Val Thr Leu Asn Val Leu
        115                 120                 125

Glu Met Thr Ser Glu Asp Leu Glu Asn Ala Leu Lys Ala Val Ile Asn
    130                 135                 140

Asp Lys Ser Tyr Lys Glu Asn Ile Met Arg Leu Ser Ser Leu His Lys
145                 150                 155                 160

Asp Arg Pro Val Glu Pro Leu Asp Leu Ala Val Phe Trp Val Glu Phe
                165                 170                 175

Val Met Arg His Lys Gly Ala Pro His Leu Arg Pro Ala Ala His Asp
            180                 185                 190

Leu Thr Trp Tyr Gln Tyr His Ser Leu Asp Val Ile Gly Phe Leu Leu
        195                 200                 205

Ala Val Val Leu Thr Val Ala Phe Ile Thr Phe Lys Cys Cys Ala Tyr
    210                 215                 220

Gly Tyr Arg Lys Cys Leu Gly Lys Lys Gly Arg Val Lys Lys Ala His
225                 230                 235                 240

Lys Ser Lys Thr His
                245

<210> SEQ ID NO 19
```

```
<211> LENGTH: 19
<212> TYPE: DNA
<213> ORGANISM: Artificial Sequence
<220> FEATURE:
<223> OTHER INFORMATION: Primer

<400> SEQUENCE: 19
tggtgtatcg attggtttt                                              19

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
catatatctg gggctagtta atc                                         23

<210> SEQ ID NO 21
<211> LENGTH: 26
<212> TYPE: DNA
<213> ORGANISM: Artificial Sequence
<220> FEATURE:
<223> OTHER INFORMATION: Primer

<400> SEQUENCE: 21
acaaggtaat taagatgaag aaagca                                      26

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
acctgagata gtggcttcct                                             20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
tttgtcttcc aattacatgc                                             20

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24
agtagatatg gaagcacttg taag                                        24

<210> SEQ ID NO 25
<211> LENGTH: 24
<212> TYPE: DNA
<213> ORGANISM: Artificial Sequence
<220> FEATURE:
<223> OTHER INFORMATION: Primer

<400> SEQUENCE: 25
```

-continued

```
tctcagtgac aagtaatta agac                                              24

<210> SEQ ID NO 26
<211> LENGTH: 19
<212> TYPE: DNA
<213> ORGANISM: Artificial Sequence
<220> FEATURE:
<223> OTHER INFORMATION: Primer

<400> SEQUENCE: 26
cattgattgg ataaaggca                                                   19

<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
aatttgggtt cttacatatc aa                                               22

<210> SEQ ID NO 28
<211> LENGTH: 18
<212> TYPE: DNA
<213> ORGANISM: Artificial Sequence
<220> FEATURE:
<223> OTHER INFORMATION: Primer

<400> SEQUENCE: 28
gagtgaggga ggacagag                                                    18

<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
ataagtacac gccttctttt g                                                21

<210> SEQ ID NO 30
<211> LENGTH: 22
<212> TYPE: DNA
<213> ORGANISM: Artificial Sequence
<220> FEATURE:
<223> OTHER INFORMATION: Primer

<400> SEQUENCE: 30
gctgctttat acaatttgct ac                                               22

<210> SEQ ID NO 31
<211> LENGTH: 22
<212> TYPE: DNA
<213> ORGANISM: Artificial Sequence
<220> FEATURE:
<223> OTHER INFORMATION: Primer

<400> SEQUENCE: 31
cgcctacgta tcatagcagt ta                                               22

<210> SEQ ID NO 32
<211> LENGTH: 22
<212> TYPE: DNA
```

```
<213> ORGANISM: Artificial Sequence
<220> FEATURE:
<223> OTHER INFORMATION: Primer

<400> SEQUENCE: 32
ggaaagaaat tgaaatgca ac                                              22

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
tctttccgcc tactgtatca                                                20

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
ttcaagaagg gcagttttat                                                20

<210> SEQ ID NO 35
<211> LENGTH: 17
<212> TYPE: DNA
<213> ORGANISM: Artificial Sequence
<220> FEATURE:
<223> OTHER INFORMATION: Primer

<400> SEQUENCE: 35
ctctggcagg agcaaag                                                   17

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
atacacacct gggatagtgg                                                20

<210> SEQ ID NO 37
<211> LENGTH: 22
<212> TYPE: DNA
<213> ORGANISM: Artificial Sequence
<220> FEATURE:
<223> OTHER INFORMATION: Primer

<400> SEQUENCE: 37
ggtaattaag atgaagaaag ca                                             22

<210> SEQ ID NO 38
<211> LENGTH: 19
<212> TYPE: DNA
<213> ORGANISM: Artificial Sequence
<220> FEATURE:
<223> OTHER INFORMATION: Primer

<400> SEQUENCE: 38
ctgagatagt ggcttcctg                                                 19
```

<210> SEQ ID NO 39
<211> LENGTH: 17
<212> TYPE: DNA
<213> ORGANISM: Artificial Sequence
<220> FEATURE:
<223> OTHER INFORMATION: Primer

<400> SEQUENCE: 39
gtggctcaat gacaagg                                                17

<210> SEQ ID NO 40
<211> LENGTH: 23
<212> TYPE: DNA
<213> ORGANISM: Artificial Sequence
<220> FEATURE:
<223> OTHER INFORMATION: Primer

<400> SEQUENCE: 40
atatggaagc acttgtaagt aaa                                         23

<210> SEQ ID NO 41
<211> LENGTH: 22
<212> TYPE: DNA
<213> ORGANISM: Artificial Sequence
<220> FEATURE:
<223> OTHER INFORMATION: Primer

<400> SEQUENCE: 41
ttaagacgaa ggaaacaatt ct                                          22

<210> SEQ ID NO 42
<211> LENGTH: 19
<212> TYPE: DNA
<213> ORGANISM: Artificial Sequence
<220> FEATURE:
<223> OTHER INFORMATION: Primer

<400> SEQUENCE: 42
acctgagata gtggcttcc                                              19

<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43
atcaaagggt aaaattcaga                                             20

<210> SEQ ID NO 44
<211> LENGTH: 18
<212> TYPE: DNA
<213> ORGANISM: Artificial Sequence
<220> FEATURE:
<223> OTHER INFORMATION: Primer

<400> SEQUENCE: 44
ggcagtccaa aagaaata                                               18

<210> SEQ ID NO 45
<211> LENGTH: 18
<212> TYPE: DNA
<213> ORGANISM: Artificial Sequence
<220> FEATURE:

```
<223> OTHER INFORMATION: Primer

<400> SEQUENCE: 45
ttttgagggc aggttcta                                                    18

<210> SEQ ID NO 46
<211> LENGTH: 22
<212> TYPE: DNA
<213> ORGANISM: Artificial Sequence
<220> FEATURE:
<223> OTHER INFORMATION: Primer

<400> SEQUENCE: 46
aatgggacaa atgtaaatga ta                                               22

<210> SEQ ID NO 47
<211> LENGTH: 17
<212> TYPE: DNA
<213> ORGANISM: Artificial Sequence
<220> FEATURE:
<223> OTHER INFORMATION: Primer

<400> SEQUENCE: 47
ttctctcatg gctcgca                                                     17

<210> SEQ ID NO 48
<211> LENGTH: 24
<212> TYPE: DNA
<213> ORGANISM: Artificial Sequence
<220> FEATURE:
<223> OTHER INFORMATION: Primer

<400> SEQUENCE: 48
atgtcaaatc acaattcagt aagg                                             24

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
ccgcctactg tatcatagca                                                  20

<210> SEQ ID NO 50
<211> LENGTH: 21
<212> TYPE: DNA
<213> ORGANISM: Artificial Sequence
<220> FEATURE:
<223> OTHER INFORMATION: Primer

<400> SEQUENCE: 50
caacgaaatg tcaaatcaca g                                                21

<210> SEQ ID NO 51
<211> LENGTH: 17
<212> TYPE: DNA
<213> ORGANISM: Artificial Sequence
<220> FEATURE:
<223> OTHER INFORMATION: Primer

<400> SEQUENCE: 51
ctctggcagg agcaaag                                                     17
```

<210> SEQ ID NO 52
<211> LENGTH: 17
<212> TYPE: DNA
<213> ORGANISM: Artificial Sequence
<220> FEATURE:
<223> OTHER INFORMATION: Primer

<400> SEQUENCE: 52
acagtgggca gagacag                                                   17

<210> SEQ ID NO 53
<211> LENGTH: 18
<212> TYPE: DNA
<213> ORGANISM: Artificial Sequence
<220> FEATURE:
<223> OTHER INFORMATION: Primer

<400> SEQUENCE: 53
gtggtttatt ccccgtat                                                  18

<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
atacacacct gggatagtgg                                                20

<210> SEQ ID NO 55
<211> LENGTH: 22
<212> TYPE: DNA
<213> ORGANISM: Artificial Sequence
<220> FEATURE:
<223> OTHER INFORMATION: Primer

<400> SEQUENCE: 55
ggtaattaag atgaagaaag ca                                             22

<210> SEQ ID NO 56
<211> LENGTH: 18
<212> TYPE: DNA
<213> ORGANISM: Artificial Sequence
<220> FEATURE:
<223> OTHER INFORMATION: Primer

<400> SEQUENCE: 56
gaaatggcat aggttgtc                                                  18

<210> SEQ ID NO 57
<211> LENGTH: 17
<212> TYPE: DNA
<213> ORGANISM: Artificial Sequence
<220> FEATURE:
<223> OTHER INFORMATION: Primer

<400> SEQUENCE: 57
ggccacactc aactgta                                                   17

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
ctcaaaaaaa acacagtagg                                              20

<210> SEQ ID NO 59
<211> LENGTH: 18
<212> TYPE: DNA
<213> ORGANISM: Artificial Sequence
<220> FEATURE:
<223> OTHER INFORMATION: Primer

<400> SEQUENCE: 59 acttttctg cccttat                                                  18

<210> SEQ ID NO 60
<211> LENGTH: 23
<212> TYPE: DNA
<213> ORGANISM: Artificial Sequence
<220> FEATURE:
<223> OTHER INFORMATION: Primer

<400> SEQUENCE: 60
atatggaagc acttgtaagt aaa                                          23

<210> SEQ ID NO 61
<211> LENGTH: 22
<212> TYPE: DNA
<213> ORGANISM: Artificial Sequence
<220> FEATURE:
<223> OTHER INFORMATION: Primer

<400> SEQUENCE: 61
ttaagacgaa ggaaacaatt ct                                           22

<210> SEQ ID NO 62
<211> LENGTH: 17
<212> TYPE: DNA
<213> ORGANISM: Artificial Sequence
<220> FEATURE:
<223> OTHER INFORMATION: Primer

<400> SEQUENCE: 62
aatggcatac gttgtca                                                 17

<210> SEQ ID NO 63
<211> LENGTH: 19
<212> TYPE: DNA
<213> ORGANISM: Artificial Sequence
<220> FEATURE:
<223> OTHER INFORMATION: Primer

<400> SEQUENCE: 63
agaatggcaa ttatgaaca                                               19

<210> SEQ ID NO 64
<211> LENGTH: 18
<212> TYPE: DNA
<213> ORGANISM: Artificial Sequence
<220> FEATURE:
<223> OTHER INFORMATION: Primer

<400> SEQUENCE: 64
tgtgtgccct taaagtct                                                18

<210> SEQ ID NO 65
<211> LENGTH: 19

<210> SEQ ID NO 65
<211> LENGTH: 19
<212> TYPE: DNA
<213> ORGANISM: Artificial Sequence
<220> FEATURE:
<223> OTHER INFORMATION: Primer

<400> SEQUENCE: 65
agaatggcaa ttatgaaca                                        19

<210> SEQ ID NO 66
<211> LENGTH: 19
<212> TYPE: DNA
<213> ORGANISM: Artificial Sequence
<220> FEATURE:
<223> OTHER INFORMATION: Primer

<400> SEQUENCE: 66
acctgagata gtggcttcc                                        19

<210> SEQ ID NO 67
<211> LENGTH: 17
<212> TYPE: DNA
<213> ORGANISM: Artificial Sequence
<220> FEATURE:
<223> OTHER INFORMATION: Primer

<400> SEQUENCE: 67
ctctggctct gtcctac                                          17

<210> SEQ ID NO 68
<211> LENGTH: 19
<212> TYPE: DNA
<213> ORGANISM: Artificial Sequence
<220> FEATURE:
<223> OTHER INFORMATION: Primer

<400> SEQUENCE: 68
acctgagata gtggcttcc                                        19

<210> SEQ ID NO 69
<211> LENGTH: 20
<212> TYPE: DNA
<213> ORGANISM: Artificial Sequence
<220> FEATURE:
<223> OTHER INFORMATION: Primer

<400> SEQUENCE: 69
atcaaagggt aaaattcaga                                       20

<210> SEQ ID NO 70
<211> LENGTH: 18
<212> TYPE: DNA
<213> ORGANISM: Artificial Sequence
<220> FEATURE:
<223> OTHER INFORMATION: Primer

<400> SEQUENCE: 70
cagcagcttg tcacctac                                         18

<210> SEQ ID NO 71
<211> LENGTH: 20
<212> TYPE: DNA
<213> ORGANISM: Artificial Sequence
<220> FEATURE:
<223> OTHER INFORMATION: Primer

<400> SEQUENCE: 71
aatttgcttt tgaaagaatc                                               20

<210> SEQ ID NO 72
<211> LENGTH: 18
<212> TYPE: DNA
<213> ORGANISM: Artificial Sequence
<220> FEATURE:
<223> OTHER INFORMATION: Primer

<400> SEQUENCE: 72
ggtaggccca aatactca                                                 18

<210> SEQ ID NO 73
<211> LENGTH: 20
<212> TYPE: DNA
<213> ORGANISM: Artificial Sequence
<220> FEATURE:
<223> OTHER INFORMATION: Primer

<400> SEQUENCE: 73
aatttgcttt tgaaagaatc                                               20

<210> SEQ ID NO 74
<211> LENGTH: 18
<212> TYPE: DNA
<213> ORGANISM: Artificial Sequence
<220> FEATURE:
<223> OTHER INFORMATION: Primer

<400> SEQUENCE: 74
ggcagtccaa aagaaata                                                 18

<210> SEQ ID NO 75
<211> LENGTH: 18
<212> TYPE: DNA
<213> ORGANISM: Artificial Sequence
<220> FEATURE:
<223> OTHER INFORMATION: Primer

<400> SEQUENCE: 75
ttttgagggc aggttcta                                                 18

<210> SEQ ID NO 76
<211> LENGTH: 18
<212> TYPE: DNA
<213> ORGANISM: Artificial Sequence
<220> FEATURE:
<223> OTHER INFORMATION: Primer

<400> SEQUENCE: 76
cacctctggc atgactac                                                 18

<210> SEQ ID NO 77
<211> LENGTH: 19
<212> TYPE: DNA
<213> ORGANISM: Artificial Sequence
<220> FEATURE:
<223> OTHER INFORMATION: Primer

<400> SEQUENCE: 77
ttgcaggagt ttgtttaat                                                19

<210> SEQ ID NO 78
<211> LENGTH: 22
<212> TYPE: DNA
<213> ORGANISM: Artificial Sequence

```
<220> FEATURE:
<223> OTHER INFORMATION: Primer

<400> SEQUENCE: 78
aatgggacaa atgtaaatga ta                                              22

<210> SEQ ID NO 79
<211> LENGTH: 19
<212> TYPE: DNA
<213> ORGANISM: Artificial Sequence
<220> FEATURE:
<223> OTHER INFORMATION: Primer

<400> SEQUENCE: 79
cattgcagga gtttgttta                                                  19

<210> SEQ ID NO 80
<211> LENGTH: 20
<212> TYPE: DNA
<213> ORGANISM: Artificial Sequence
<220> FEATURE:
<223> OTHER INFORMATION: Primer

<400> SEQUENCE: 80
catctgagaa ccctaagaga                                                 20

<210> SEQ ID NO 81
<211> LENGTH: 20
<212> TYPE: DNA
<213> ORGANISM: Artificial Sequence
<220> FEATURE:
<223> OTHER INFORMATION: Primer

<400> SEQUENCE: 81
agaaatagcc tctgaaattc                                                 20

<210> SEQ ID NO 82
<211> LENGTH: 24
<212> TYPE: DNA
<213> ORGANISM: Artificial Sequence
<220> FEATURE:
<223> OTHER INFORMATION: Primer

<400> SEQUENCE: 82
atgtcaaatc acaattcagt aagg                                            24

<210> SEQ ID NO 83
<211> LENGTH: 20
<212> TYPE: DNA
<213> ORGANISM: Artificial Sequence
<220> FEATURE:
<223> OTHER INFORMATION: Primer

<400> SEQUENCE: 83
ccgcctactg tatcatagca                                                 20

<210> SEQ ID NO 84
<211> LENGTH: 21
<212> TYPE: DNA
<213> ORGANISM: Artificial Sequence
<220> FEATURE:
<223> OTHER INFORMATION: Primer

<400> SEQUENCE: 84
gagtgtacga ggttgagtaa g                                               21
```

```
<210> SEQ ID NO 85
<211> LENGTH: 21
<212> TYPE: DNA
<213> ORGANISM: Artificial Sequence
<220> FEATURE:
<223> OTHER INFORMATION: Primer

<400> SEQUENCE: 85
attttgccag tatcttttta g                                          21

<210> SEQ ID NO 86
<211> LENGTH: 21
<212> TYPE: DNA
<213> ORGANISM: Artificial Sequence
<220> FEATURE:
<223> OTHER INFORMATION: Primer

<400> SEQUENCE: 86
caacgaaatg tcaaatcaca g                                          21

<210> SEQ ID NO 87
<211> LENGTH: 27
<212> TYPE: DNA
<213> ORGANISM: Homo sapiens

<400> SEQUENCE: 87
catcagagac agagcatttt acacctt                                    27

<210> SEQ ID NO 88
<211> LENGTH: 26
<212> TYPE: DNA
<213> ORGANISM: Homo sapiens

<400> SEQUENCE: 88
ggacctattg agccctgcat ctgtct                                     26

<210> SEQ ID NO 89
<211> LENGTH: 25
<212> TYPE: DNA
<213> ORGANISM: Homo sapiens

<400> SEQUENCE: 89
ggttcccctg ccgcggctgg ccaca                                      25

<210> SEQ ID NO 90
<211> LENGTH: 22
<212> TYPE: DNA
<213> ORGANISM: Homo sapiens

<400> SEQUENCE: 90
gccctgggct gaaagtggaa ag                                         22

<210> SEQ ID NO 91
<211> LENGTH: 23
<212> TYPE: DNA
<213> ORGANISM: Homo sapiens

<400> SEQUENCE: 91
atgcgggagg ccttgcggga gct                                        23

<210> SEQ ID NO 92
<211> LENGTH: 24
<212> TYPE: DNA
<213> ORGANISM: Homo sapiens
```

<400> SEQUENCE: 92
ctctgcgcgg cggtgctggc taag                                              24

<210> SEQ ID NO 93
<211> LENGTH: 25
<212> TYPE: DNA
<213> ORGANISM: Homo sapiens

<400> SEQUENCE: 93
taccccaggc caatcatgcc caaca                                             25

<210> SEQ ID NO 94
<211> LENGTH: 27
<212> TYPE: DNA
<213> ORGANISM: Homo sapiens

<400> SEQUENCE: 94
tccaggcaaa atacttttta aaaaatg                                           27

<210> SEQ ID NO 95
<211> LENGTH: 23
<212> TYPE: DNA
<213> ORGANISM: Homo sapiens

<400> SEQUENCE: 95
agcatgcggg aggcctcgcg gga                                               23

<210> SEQ ID NO 96
<211> LENGTH: 21
<212> TYPE: DNA
<213> ORGANISM: Homo sapiens

<400> SEQUENCE: 96
gcgggagctc catgcgagag g                                                 21

<210> SEQ ID NO 97
<211> LENGTH: 25
<212> TYPE: DNA
<213> ORGANISM: Homo sapiens

<400> SEQUENCE: 97
tggtggtcct caccccggag gtgaa                                             25

<210> SEQ ID NO 98
<211> LENGTH: 26
<212> TYPE: DNA
<213> ORGANISM: Homo sapiens

<400> SEQUENCE: 98
tacatcaaag aggagaactt tttcac                                            26

<210> SEQ ID NO 99
<211> LENGTH: 26
<212> TYPE: DNA
<213> ORGANISM: Homo sapiens

<400> SEQUENCE: 99
tgatcaggca cctgaatgct acttcc                                            26

<210> SEQ ID NO 100
<211> LENGTH: 21
<212> TYPE: DNA

-continued

<213> ORGANISM: Homo sapiens

<400> SEQUENCE: 100
acctctgcgg ggcggtgctg g                                           21

<210> SEQ ID NO 101
<211> LENGTH: 23
<212> TYPE: DNA
<213> ORGANISM: Homo sapiens

<400> SEQUENCE: 101
aagaacatgc tttaccctct ggc                                         23

<210> SEQ ID NO 102
<211> LENGTH: 18
<212> TYPE: DNA
<213> ORGANISM: Homo sapiens

<400> SEQUENCE: 102
ctctggctct gtcctacc                                               18

<210> SEQ ID NO 103
<211> LENGTH: 24
<212> TYPE: DNA
<213> ORGANISM: Homo sapiens

<400> SEQUENCE: 103
tcctaccttt gctatgctgt ttct                                        24

<210> SEQ ID NO 104
<211> LENGTH: 17
<212> TYPE: DNA
<213> ORGANISM: Homo sapiens

<400> SEQUENCE: 104
tgtcagtggt ggatatt                                                17

<210> SEQ ID NO 105
<211> LENGTH: 16
<212> TYPE: DNA
<213> ORGANISM: Homo sapiens

<400> SEQUENCE: 105
ggtggatctt ctcagc                                                 16

<210> SEQ ID NO 106
<211> LENGTH: 13
<212> TYPE: DNA
<213> ORGANISM: Homo sapiens

<400> SEQUENCE: 106
tcagctatgc atc                                                    13

<210> SEQ ID NO 107
<211> LENGTH: 21
<212> TYPE: DNA
<213> ORGANISM: Homo sapiens

<400> SEQUENCE: 107
gcatccgtgt ggctgttccg a                                           21

<210> SEQ ID NO 108
<211> LENGTH: 20

<212> TYPE: DNA
<213> ORGANISM: Homo sapiens

<400> SEQUENCE: 108
tggctgttcc gacgggactt                                              20

<210> SEQ ID NO 109
<211> LENGTH: 16
<212> TYPE: DNA
<213> ORGANISM: Homo sapiens

<400> SEQUENCE: 109
gggacttcgt gatgga                                                  16

<210> SEQ ID NO 110
<211> LENGTH: 23
<212> TYPE: DNA
<213> ORGANISM: Homo sapiens

<400> SEQUENCE: 110
gtgatggact accccaggcc gat                                          23

<210> SEQ ID NO 111
<211> LENGTH: 25
<212> TYPE: DNA
<213> ORGANISM: Homo sapiens

<400> SEQUENCE: 111
cctgcctcct tcgcgcattt cagag                                        25

<210> SEQ ID NO 112
<211> LENGTH: 25
<212> TYPE: DNA
<213> ORGANISM: Homo sapiens

<400> SEQUENCE: 112
gcgatcattc ctgactgctc ctcag                                        25

<210> SEQ ID NO 113
<211> LENGTH: 22
<212> TYPE: DNA
<213> ORGANISM: Homo sapiens

<400> SEQUENCE: 113
ccctggagca tgcattcagc ag                                           22

<210> SEQ ID NO 114
<211> LENGTH: 23
<212> TYPE: DNA
<213> ORGANISM: Homo sapiens

<400> SEQUENCE: 114
cattcagcag cagcccagac cct                                          23

<210> SEQ ID NO 115
<211> LENGTH: 23
<212> TYPE: DNA
<213> ORGANISM: Homo sapiens

<400> SEQUENCE: 115
tacttcttcc acgtactata tta                                          23

<210> SEQ ID NO 116

```
<211> LENGTH: 24
<212> TYPE: DNA
<213> ORGANISM: Homo sapiens

<400> SEQUENCE: 116
ggcctccttc cactatatgt gtgt                                              24

<210> SEQ ID NO 117
<211> LENGTH: 21
<212> TYPE: DNA
<213> ORGANISM: Homo sapiens

<400> SEQUENCE: 117
ggagagagta cggaaccaca t                                                 21

<210> SEQ ID NO 118
<211> LENGTH: 23
<212> TYPE: DNA
<213> ORGANISM: Homo sapiens

<400> SEQUENCE: 118
tcaatttggt tattgcgaac tga                                               23

<210> SEQ ID NO 119
<211> LENGTH: 22
<212> TYPE: DNA
<213> ORGANISM: Homo sapiens

<400> SEQUENCE: 119 cagggggaata gcttgccact at                                               22

<210> SEQ ID NO 120
<211> LENGTH: 24
<212> TYPE: DNA
<213> ORGANISM: Homo sapiens

<400> SEQUENCE: 120
tgttgcgaac ggactttgtt ttgg                                              24

<210> SEQ ID NO 121
<211> LENGTH: 22
<212> TYPE: DNA
<213> ORGANISM: Homo sapiens

<400> SEQUENCE: 121
ttcaccatgc aatcggtggt gg                                                22

<210> SEQ ID NO 122
<211> LENGTH: 25
<212> TYPE: DNA
<213> ORGANISM: Homo sapiens

<400> SEQUENCE: 122
ctagaaatag cttctgaaat tctcc                                             25

<210> SEQ ID NO 123
<211> LENGTH: 24
<212> TYPE: DNA
<213> ORGANISM: Homo sapiens

<400> SEQUENCE: 123
cggcatatga tatctacagt caca                                              24
```

-continued

```
<210> SEQ ID NO 124
<211> LENGTH: 24
<212> TYPE: DNA
<213> ORGANISM: Homo sapiens

<400> SEQUENCE: 124
tcaatttggt tgctgcgaac ggac                                              24
```

GENOTYPING THE HUMAN UDP-GLUCURONOSYLTRANSFERASE 1 (UGT1) GENE

CROSS REFERENCE TO RELATED APPLICATION

This application claims the benefit of earlier filed U.S. Provisional Application Ser. No. 60/084,807, filed May 7, 1998.

INTRODUCTION

The metabolic processes commonly involved in the biotransformation of xenobiotics have been classified into functionalization reactions (phase I reactions), in which lipophilic compounds are modified via monooxygenation, dealkylation, reduction, aromatization, or hydrolysis. These modified molecules can then be substrates for the phase II reactions, often called conjugation reactions, as they conjugate a functional group with a polar, endogenous compound. Drug glucuronidation, a major phase II conjugation reaction in the mammalian detoxification system, is catalyzed by the UDP-glucuronosyltransferases (UGTs) (Batt AM, et al. (1994) Clin Chim Acta 226:171–190; Burchell et al. (1995) Life Sci. 57:1819-31).

The UGTs are a family of enzymes that catalyze the glucuronic acid conjugation of a wide range of endogenous and exogenous substrates including phenols, alcohols, amines and fatty acids. The reactions catalyzed by UGTs permit the conversion of a large range of toxic endogenous/xenobiotic compounds to more water-soluble forms for subsequent excretion (Parkinson A (1996) Toxicol Pathol 24:48–57).

The UGT isoenzymes are located primarily in hepatic endoplasmic reticulum and nuclear envelope (Parkinson A (1996) Toxicol Pathol 24:48–57), though they are also expressed in other tissues such as kidney and skin. UGTs are encoded by a large multigene superfamily that has evolved to produce catalysts with differing but overlapping substrate specificities. Three families, UGT1, UGT2, and UGT8, have been identified within the superfamily. UGTs are assigned to one of the subfamilies based on amino acid sequence identity, e.g., UGT1 family members have greater than 45% amino acid sequence identity (Mackenzie et al. 1997) Pharmacogenetics 7:255-69).

The UGT1 locus is located on chromosome 2q37, and contains at least 12 promoters/first exons, which are apparently able to splice with common exons 2 through 5, producing gene products having strikingly different N-terminal halves (amino acid sequence identities ranging from 24% to 49%), but identical C-terminal halves (FIG. 1). At least eight different isoenzymes are encoded by the UGT1 locus; at least one or more first exons encode pseudogenes. The different N-terminal halves encoded by the first exons confer different substrate binding specificities upon the UGT1 isoenzymes, while exons 2–5, which are present in all UGT1 isoenzyme mRNAs, encode the UDP-glucuronic acid binding domain, membrane anchorage site, and ER retention signal that are common to all UGT proteins (Ritter et al. (1992) J Biol Chem 267:3257–3261). UGT1 locus isoenzymes are best known for their role in glucoronidation and metabolism of many substrates, including bilirubin (1A1, 1 D1), planar and non-planar phenols, naphthols (1F1) (Ouzzine M, et al. (1994) Arch Biochem Biophys 310:196–204), anthraquinones, flavones, aliphatic alcohols, aromatic carboxylic acids, and steroids (Ebner T, et al. (1993) Drug Metab Dispos 21:50–55).

In addition to UGT1 exon usage, metabolism of endogenous and exogenous substrates can also be affected by competitive binding phenomena. For example, in some cases exogenous substrates for the UGT1 enzymes have a higher binding affinity or avidity for the enzyme than the endogenous UGT1 substrates. For example, UGT1*1, the major bilirubin-metabolizing form of UGT1, more readily binds both octyl-gallate and emodin than it binds bilirubin, thus indicating the potential of these xenobiotics to cause jaundice by inhibition of bilirubin binding to UGT1*1 (where 1*1 indicates that the first exon is used in the spliced gene product). UGT1*1 is also responsible for glucuronidation of the oral contraceptive ethinylestradiol (Ebner et al. (1993) Mol. Pharmacol. 43:649-54), and can also glucuronidate phenols, anthroquinones, flavones, and certain endogenous steroids.

As noted above, the first exon present in UGT1 can affect substrate binding specificity of the UGT1 gene product (for a review, see Burchell (1995) Life Sci. 57:1819-31). For example, UGT1*2 accepts a wide range of compounds as substrates including non-planar phenols, anthraquinones, flavones, aliphatic alcohols, aromatic carboxylic acids, steroids (4-hydroxyestrone, estrone) and many drugs of varied structure (Ebner et al. (1993) Drug. Metab. Disp. 21:50-5; Burchell (1995) Life Sci. 57:1 819-31). In contrast, UGT1*6 exhibits only limited substrate specificity for planar phenolic compounds relative to other human UGTs.

Polymorphisms can markedly affect binding of the endogenous substrate, which can be manifested as clinical syndromes. At least two conditions, Crigler-Najjar syndrome and Gilbert syndrome, are associated with UGT1 polymorphisms. Both of these syndromes are hereditary and are associated with predominantly unconjugated hyperbilirubinemia. Crigler-Najjar syndrome is associated with intense, persistent jaundice which begins at birth. Some affected infants die in the first weeks or months of life with kernicterus; others survive with little or no neurologic defect. Crigler-Najjar syndrome is caused by a defect in the ability of UGT1 to catalyze UDP-glucuronidation of bilirubin, resulting in accumulation of bilirubin in the blood (Erps et al. (1994) J. Clin. Invest. 93:564-70). Gilbert syndrome is a benign mild form of unconjugated hyperbilirubinemia that is characterized by normal liver function tests, normal liver histology, delayed clearance of bilirubin from the blood, and mild jaundice that tends to fluctuate in severity. As with Crigler-Najjar syndrome, Gilbert syndrome is associated with a defect in UGT1. Specific UGT polymorphisms that are known to be associated with disease are indicated in FIG. 1.

Alteration of the expression or function of UGTs may also affect drug metabolism. For example, there may be common polymorphisms in the human UGT1 gene that alter expression or function of the protein product and cause drug exposure-related phenotypes. Thus, there is a need in the field to identify UGT1 polymorphisms in order to provide a better understanding of drug metabolism and the diagnosis of drug exposure-related phenotypes.

RELEVANT LITERATURE

Genbank accession number M84122 provides UGT1 exon 2, M84123 provides exons 3 and 4, M84124 provides 5, M84125 provides exon 1A, M84127 provides exon 1C, M84128 provides exon 1D, M84129 provides exon 1E, M84130 provides exon 1F, U39570 provides exon 1G, U42604 provides exon 1H, U39550 provides exon 1J.

The UGT gene superfamily and recommended nomenclature for describing UGT genes and alleles are reviewed in Mackenzie et al. (1997) Pharmacogenet. 7:255-69.

The two UGT1A6 genetic polymorphisms are described in Ciotti et al. (1997) *Am. J. Hum. Genet.* 61(Supp):A249. The identification of Asp446 as a critical residue in UGT1 is described in Iwano et al. (1997) *Biochem. J.* 325:587-91.

A review of the substrate specificity of human UDP-glucuronosyltransferases is provided by Burchell et al. (1995) *Life Sci.* 57:1819-31. For a review of drug glucoronidation in humans, see Miners et al. (1991) *Pharmacol. Ther.* 51:347-69.

At least twelve UGT1A1 polymorphisms have been identified and linked to disease. These UGT1A1 alleles, each of described in OMIM Entry 191740 and in OMIM Entry 143500 include:

1) UGT1*FB (UGT1A1, 13-BP DEL, EX2; 191740.0001), which contains a 13 bp deletion in exon 2 and is associated with Crigler-Najjar syndrome type I (CN-I);

2) UGT1A1, EXON4, C-T, SER-PHE (191740.0002), which contains a C-to-T transition in exon 4 (resulting in an amino acid change from serine to phenylalanine) is associated with CN-I and deficiency of both bilirubin-UGT and phenol-UGT activities in the liver;

3) UGT1A1, GLN331TER (191740.0003), which contains a C-to-T transition 6 bp upstream from the 3-prime end of exon 2 of the common region (replacement of a glutamine codon with a stop codon), is associated with CN-I;

4) UGT1A1, ARG341TER (191740.0004), which contains a nonsense mutation (CGA-to-TGA) in exon 3 and is associated with CN-I and a total absence of all phenol/bilirubin UGT proteins and their activities in liver homogenate by enzymologic and immunochemical analysis;

5) UGT1A1, GLN331ART (191740.0005), which contains an A-to-G transition 5 bp upstream of the exon 2/intron 2 boundary (resulting in a glutamine-to-arginine substitution), is associated with Crigler-Najjar Syndrome, type II (CN-II);

6) UGT1A1, PHE170DEL (191740.0006), which contains a deletion of the phenylalanine codon at position 170 in exon 1, and is associated with CN-I;

7) UGT1A1, SER376PHE (191740.0007), which contains a C-to-T transition in codon 376 (resulting in a change of serine to phenylalanine) and is associated with CN-I;

8) UGT1A1, GLY309GLU (191740.0008), which contains a G-to-A transition in codon 309 (resulting in a glycine to glutamic acid change) and is associated with CN-I;

9) UGT1A1, NT840, C-A, CYS-TER (191740.0009), which contains a C-to-A transversion at base position 840 in exon 1 (resulting in replacing a cysteine with a stop codon), is associated with CN-I;

10) UGT1A1, PRO229GLN (191740.00010), which contains C-to-A transversion at nucleotide 686 (changing proline-229 to glutamine), is associated with Gilbert syndrome;

11) UGT1A1, 2-BP INS, TA INS, TATAA ELEMENT (191740.00011) contains 2 extra bases (TA) in the TATAA element of the 5-prime promoter region of the gene (where normally an A(TA)6TAA element is present between nucleotides −23 and −3) and is associated with Gilbert syndrome; and 12) UGT1A1, 1-BP INS, 470T INS (191740.00012), which contains 470insT mutation in exon 1 and is associated with CN-I.

SUMMARY OF THE INVENTION

Genetic sequence polymorphisms are identified in the UGT1 gene. Nucleic acids comprising the polymorphic sequences are used in screening assays, and for genotyping individuals. The genotyping information is used to predict an individuals' rate of metabolism for UGT1 substrates., potential drug-drug interactions, and adverse/side effects.

Accordingly, in one aspect the invention features an isolated nucleic acid molecule comprising a UGT1 sequence polymorphism of SEQ ID NOS:87–124, as part of other than a naturally occurring chromosome. In related aspects, the invention features nucleic acid probes for detection of UGT1 locus polymorphisms, where the probe comprises a polymorphic sequence of SEQ ID NOS:87–124.

In another aspect the invention features an array of oligonucleotides comprising two or more probes for detection of UGT1 locus polymorphisms, where the probes comprise at least one form of a polymorphic sequences of SEQ ID NOS:87–124.

In still another aspect, the invention features a method for detecting in an individual a polymorphism in UGT1 metabolism of a substrate, where the method comprises analyzing the genome of the individual for the presence of at least one UGT1 polymorphism of SEQ ID NOS:87–124; wherein the presence of the predisposing polymorphism is indicative of an alteration in UGT1 expression or activity.

In one embodiment, the analyzing step of the method is accomplished by detection of specific binding between the individual's genomic DNA with an array of oligonucleotides comprising two or more probes for detection of UGT1 locus polymorphisms, where the probes comprise at least one form of a polymorphic sequence of SEQ ID NOS:87–124.

In other embodiments of the method, the alteration is UGT1 expression or activity is tissue specific, or is in response to a UGT1 modifier. The UGT1 modifier may either induce or inhibit UGT1 expression.

BRIEF DESCRIPTION OF THE SEQUENCE LISTING

Figure 1:
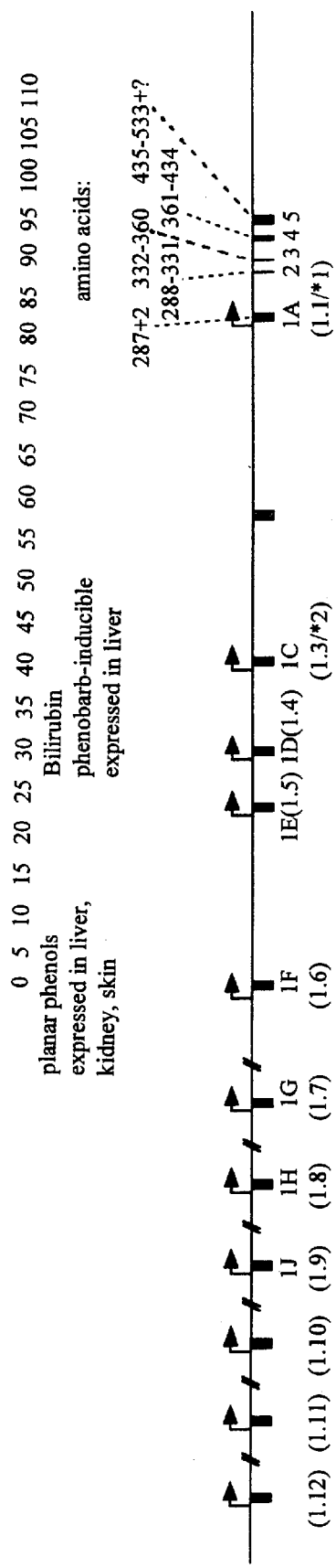
FIG. 1 is a schematic showing the UGT1 locus. Each of the first exons is denoted by both its alphabetic and numerical nomenclatures (e.g., 1A and 1.1).

UGT1Reference Sequences. SEQ ID NOS: 1, 3, 5, 7, 9, 11, 13, and 15 are the UGT1 reference polynucleotide sequences for UGT1 exons 1A, 1C, 1D, 1E, 1F, 1G, 1H, and 1J. The polypeptide sequences are encoded by these reference exon sequences are SEQ ID NOS:2, 4, 6, 8,12,14, and 16. SEQ ID NOS: 17 and 18 are the reference polynucleotide and amino acid sequences for UGT1 exons 2–5.

PCR Primers The primary and secondary PCR primers for amplification of polymorphic sequences are presented as SEQ ID NOS:19–50.

Sequencing Primers. The primers used in sequencing isolated polymorphic sequences are presented as SEQ ID NOS:51–86.

Polymorphisms. Polymorphic sequences of the invention are presented as SEQ ID NOS:88–124.

DESCRIPTION OF THE SPECIFIC EMBODIMENTS

Pharmacogenetics is the linkage between an individual's genotype and that individual's ability to metabolize or react to a therapeutic agent. Differences in metabolism or target sensitivity can lead to severe toxicity or therapeutic failure by altering the relation between bioactive dose and blood concentration of the drug. Relationships between polymorphisms in metabolic enzymes or drug targets and both response and toxicity can be used to optimize therapeutic dose administration.

Genetic polymorphisms are identified in the UGT1 gene. Nucleic acids comprising the polymorphic sequences are used to screen patients for altered metabolism for UGT1 substrates, potential drug-drug interactions, and adverse/side effects, as well as diseases that result from environmental or occupational exposure to toxins. The nucleic acids are used to establish animal, cell culture and in vitro cell-free models for drug metabolism.

Definitions

It is to be understood that this invention is not limited to the particular methodology, protocols, cell lines, animal species or genera, constructs, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a construct" includes a plurality of such constructs and reference to "the UGT1 nucleic acid" includes reference to one or more nucleic acids and equivalents thereof known to those skilled in the art, and so forth. All technical and scientific terms used herein have the same meaning as commonly understood to one of ordinary skill in the art to which this invention belongs unless clearly indicated otherwise.

UGT1 polymorphic sequences. The sequence of the UGT1 gene is known in the art, and accessible in public databases, as cited above. This sequence is useful as a reference for the genomic location of the human gene, and for specific coding region sequences. As used herein, the term "UGT1 gene" is intended to refer to both the wild-type and variant sequences, unless specifically denoted otherwise. Nucleic acids of particular interest comprise the provided variant nucleotide sequence(s). For screening purposes, hybridization probes may be used where both polymorphic forms are present, either in separate reactions, or labeled such that they can be distinguished from each other. Assays may utilize nucleic acids that hybridize to one or more of the described polymorphisms.

The genomic UGT1 sequence is of particular interest. A polymorphic UGT1 gene sequence, i.e. including one or more of the provided polymorphisms, is useful for expression studies to determine the effect of the polymorphisms on enzymatic activity. The polymorphisms are also used as single nucleotide polymorphisms to detect genetic association with phenotypic variation in UGT1 activity and expression.

Figure 2:
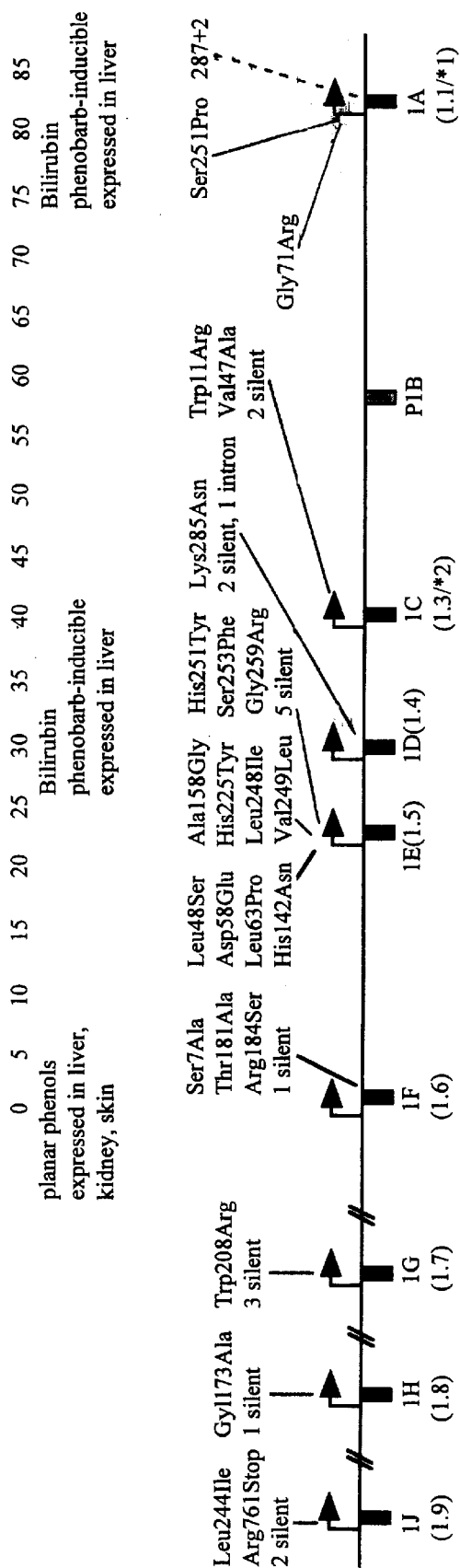
FIG. 2 is a schematic showing exons 1A-1J of the UGT1 locus and the polymorphisms described in the present application.
Figure 3:
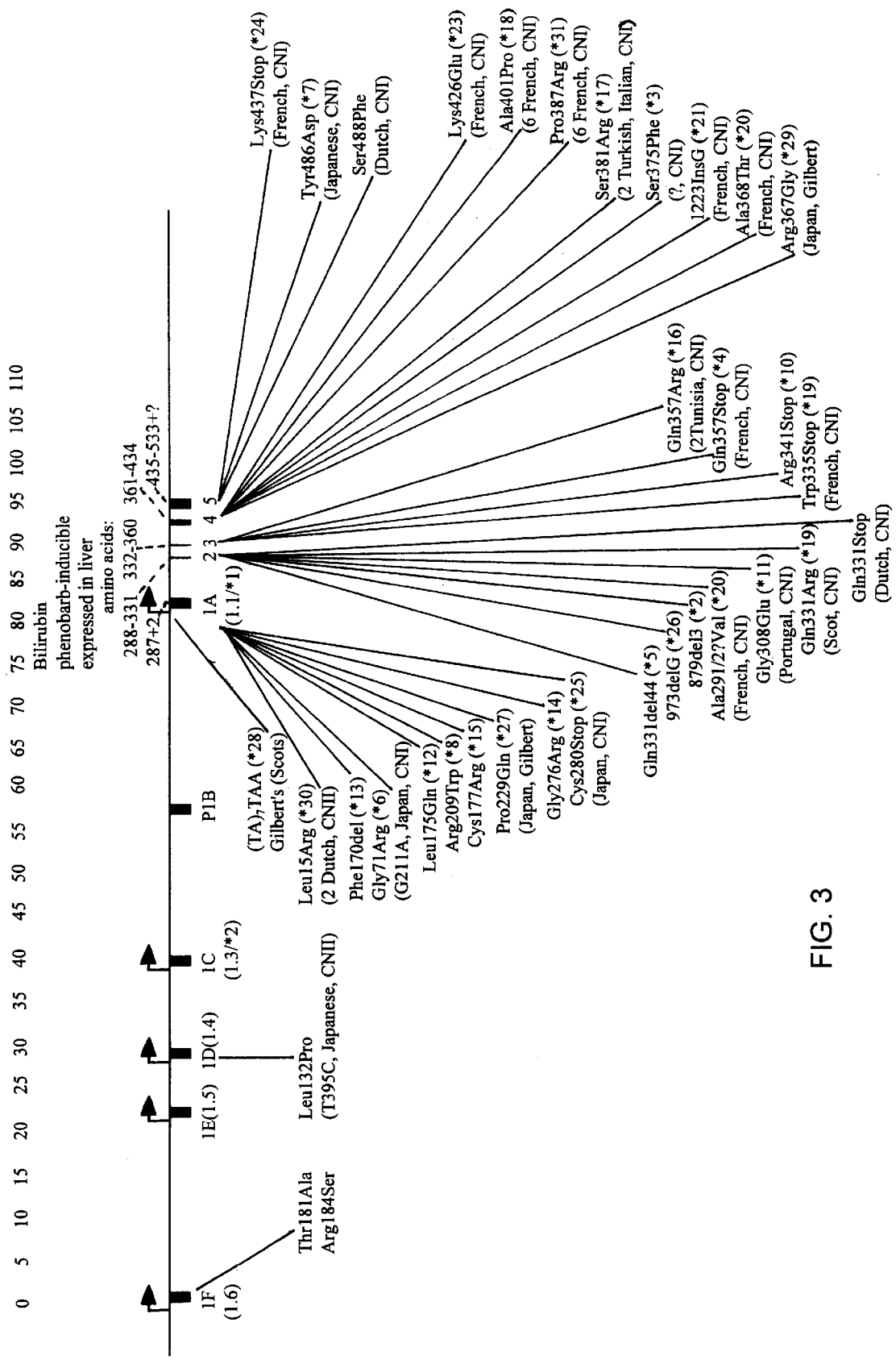
FIG. 3 is a schematic showing the exons 1A-1F, and 2–5 of the UGT1 locus and the polymorphisms that have been publicly disclosed.

The UGT1 exon structure is illustrated in FIG. 1. The UGT1 locus contains at least 12 promoters/first exons, which are apparently able to splice with common exons 2 through 5, producing gene products having different N-terminal halves but identical C-terminal halves. The first exon utilized at least in part determines the substrate specificity of the resulting UGT1 gene product. Each of the first exons in FIG. 1 is denoted by both its alphabetic and numerical nomenclatures (e.g., 1A and 1.1). Polymorphisms in the UGT1 first exon can be associated with alteration of substrate binding specificity and/or disease. FIG. 2 shows UGT1 exons 1A-1J and the polymorphisms described in the present application. FIG. 3 shows UGT1 exons 1A-1F and 2–5 and the polymorphisms in these exons that have been publicly disclosed. Polymorphisms denoted by an asterisk (*) have been assigned the indicated "allele name" (e.g., *12). The specific associated disease is indicated below in parentheses for several of these disease-associated polymorphisms. Except for the "mutation" that is associated with Gilbert's (*28, which is not universally agreed upon in the literature), all mutations in exons 1D, 1A, and 2–5 were isolated from individuals with disease.

Fragments of the DNA sequence are obtained by chemically synthesizing oligonucleotides in accordance with conventional methods, by restriction enzyme digestion, by PCR amplification, etc. For the most part, DNA fragments will be of at least 15 nt, usually at least 20 nt, often at least 50 nt. Such small DNA fragments are useful as primers for PCR, hybridization screening, etc. Larger DNA fragments, i.e. greater than 100 nt are useful for production of the encoded polypeptide, promoter motifs, etc. For use in amplification reactions, such as PCR, a pair of primers will be used. The exact composition of primer sequences is not critical to the invention, but for most applications the primers will hybridize to the subject sequence under stringent conditions, as known in the art.

The UGT1 nucleic acid sequences are isolated and obtained in substantial purity, generally as other than an intact mammalian chromosome. Usually, the DNA will be obtained substantially free of other nucleic acid sequences that do not include a UGT1 sequence or fragment thereof, generally being at least about 50%, usually at least about 90% pure and are typically "recombinant", i.e. flanked by one or more nucleotides with which it is not normally associated on a naturally occurring chromosome.

UGT1 polypeptides. The UGT1 genetic sequence, including polymorphisms, may be employed for synthesis of a complete UGT1 protein, or polypeptide fragments thereof, particularly fragments corresponding to functional domains; binding sites; etc.; and including fusions of the subject polypeptides to other proteins or parts thereof. For expression, an expression cassette may be employed, providing for a transcriptional and translational initiation region, which may be inducible or constitutive, where the coding region is operably linked under the transcriptional control of the transcriptional initiation region, and a transcriptional and translational termination region. Various transcriptional initiation regions may be employed that are functional in the expression host. The polypeptides may be expressed in prokaryotes or eukaryotes in accordance with conventional ways, depending upon the purpose for expression. Small peptides can also be synthesized in the laboratory.

Substrate. A substrate is a chemical entity that is modified by UGT1, usually under normal physiological conditions. Although the duration of drug action tends to be shortened by metabolic transformation, drug metabolism is not "detoxification". Frequently the metabolic product has greater biologic activity than the drug itself. In some cases the desirable pharmacologic actions are entirely attributable to metabolites, the administered drugs themselves being inert. Likewise, the toxic side effects of some drugs may be due in whole or in part to metabolic products.

Substrates can be either endogenous substrates (e.g., substrates normally found within the natural environment of UGT1, such as the bilirubin or other endobiotic compound) or exogenous (e.g., substrates that are not normally found within the natural environment of UGT1, such as ethinyl estradiol or other xenobiotic compound). Exemplary UGT1 substrates (i.e., substrates of wild-type UGT1 and/or UGT1 polypeptides encoded by UGT1 polymorphisms) include, but are not necessarily limited to endobiotics such as bilirubin, bilirubin monoglucoronide, bile acids, steroids, thyroxine, biogenic amines, fat-soluble vitamins, UDPGA, 17β estradiol, estriol, 2-hydroxy-estriol, T4,rT3, and the like; and xenobiotics such as hydroxylated polycyclic aromatic hydrocarbons, heterocyclics, carcinogens, plant metabolites, octyl gallate, ethinylestradiol, anthraflavic acid, quercetin, 1-naphthol, naphthylamines, 4-aminobiphenyl, benzidine, imipamine, BP-3,6-quinol, 5-hydroxy-BP, acetaminophen, vanillin, naproxen, 4-methylumbelliferone, monohalogenated phenols, propofol, 4t-pentylphenol, 4-hydroxybiphenyl, carvacrol, emodin, galangin, bulky phenols, carboxylic acids, 5-hydroxy 2AAF, 8-hydroxy 2AAF, and the like. Table 1 provides a summary of the major endobiotic and xenobiotic substrates, as well as exemplary non-substrates, of four UGT1 isoenzymes (UGT1*1 (same as UGT1A), UGT1*4 (same as UGT1D), UGT1*6 (same as UGT1F), and UGT1*02 (same as UGT1G) (see Burchell et al. 91995) *Life Sci.* 57:1819-31).

thus, compounds such as metabolites of planar aromatic compounds and phenolic antioxidants, as well as reactive oxygen species including peroxides would be expression modifiers via their effect on the electrophile responsive element. Endogenous and exogenous inducers that are capable of inducing particular UGT activities include phenobarbital, dioxin, peroxisome proliferators, rifamicin, oral contraceptive drug, carbamazepine, cigarette smoke, cabbage, brussel sprouts, polycyclic/aromatic hydrocarbons, and derivatives of indole 3-carbonil (see Burchell et al. (1995), supra, Parkinson In: "Biotransformation of Xenobiotics." Chapter 6, *Casarett & Doull's Toxicology*, 5$^{th}$ Ed., C. Klaassen, ed.)).

Pharmacokinetic parameters. Pharmacokinetic parameters provide fundamental data for designing safe and effective dosage regimens. A drug's volume of distribution, clearance, and the derived parameter, half-life, are particularly important, as they determine the degree of fluctuation between a maximum and minimum plasma concentration during a dosage interval, the magnitude of steady state concentration and the time to reach steady state plasma concentration upon chronic dosing. Parameters derived from in vivo drug administration are useful in determining the clinical effect of a particular UGT1 genotype.

Expression assay. An assay to determine the effect of a sequence polymorphism on UGT1 expression. Expression

TABLE 1

Substrate Specificity of Human Liver UGT1 Isoenzymes

| Isoenzyme | Endobiotic | Xenobiotic | Non-substrate |
|---|---|---|---|
| UGT1*1 | Bilirubin (Km 24 μm)<br>Bilirubin monoglucuronide<br>UDPGA (Km 0.41 mM)<br>17β estradiol<br>Estriol<br>2-hydrozy-estriol<br>T4,rT3 | Octyl gallate (Km 162 μm)<br>Ethinylestradiol<br>Anthraflavic acid<br>Quercetin<br>1-naphthol | Gallic acid<br>T3<br>Menthol<br>Retinoic acid<br>Clofibrate<br>Morphine<br>Propofol<br>Testosterone |
| UGT1*4 | Bilirubin? | Naphthylamines<br>4-aminobiphenyl<br>Benzide<br>Imipamine | Bilirubin?<br>Carbamazepine |
| UGT1*6 | | 1-Naphthol<br>BP-3,6-quinol<br>5-hydroxy-BP<br>Acetaminophen (Km 2 mM)<br>Vanillin<br>Naproxen<br>4-methylumbelliferone<br>Monohalogenated phenols | 4-Hydroxybiphenyl<br>Propofol<br>Galangin<br>Emodin<br>Morphine<br>Estriol<br>Estradiol<br>AZT<br>Menthol |
| UGT1*7 | UDPGA (Km 0.41 mM)<br>T4,rT3 | Propofol (Km 172 μm)<br>4t-pentylphenol<br>4-hydroxybiphenyl<br>Carvacrol<br>Emodin<br>Galangin<br>Octyl gallate (Km 158 μM)<br>Other bulky phenols<br>Acetaminophen (Km 50 mM)<br>Carboxylic acids (some)<br>5-hydroxy 2AAF<br>8-hydroxy 2AAF | Morphine<br>Estriol<br>Estradiol<br>AZT<br>Menthol<br>Chloramphenicol<br>Androsterone<br>T3 |

Modifier. A modifier is a chemical agent that modulates the action of UGT1, either through altering its enzymatic activity (enzymatic modifier) or through modulation of expression (expression modifier, e.g., by affecting transcription or translation). In some cases the modifier may also be a substrate. For example, the UGT1 gene contains an electrophile responsive element (U.S. Pat. No. 5,589,504); assays may be performed in cell-free extracts, or by transforming cells with a suitable vector. Alterations in expression may occur in the basal level that is expressed in one or more cell types, or in the effect that an expression modifier has on the ability of the gene to be inhibited or induced. Expression levels of a variant alleles are compared by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

Gel shift or electrophoretic mobility shift assay provides a simple and rapid method for detecting DNA-binding proteins (Ausubel, F. M. et al. (1989) In: Current Protocols in Molecular Biology, Vol. 2, John Wiley and Sons, New York). This method has been used widely in the study of sequence-specific DNA-binding proteins, such as transcription factors. The assay is based on the observation that complexes of protein and DNA migrate through a nondenaturing polyacrylamide gel more slowly than free DNA fragments or double-stranded oligonucleotides. The gel shift assay is performed by incubating a purified protein, or a complex mixture of proteins (such as nuclear or cell extract preparations), with an end-labeled DNA fragment containing the putative protein binding site. The reaction products are then analyzed on a nondenaturing polyacrylamide gel. The specificity of the DNA-binding protein for the putative binding site is established by competition experiments using DNA fragments or oligonucleotides containing a binding site for the protein of interest, or other unrelated DNA sequences.

Expression assays can be used to detect differences in expression of polymorphisms with respect to tissue specificity, expression level, or expression in response to exposure to various substrates, and/or timing of expression during development. For example, since UGT1A and UGT1E are expressed in liver, UGT1A and UGT1E polymorphisms could be evaluated for expression in tissues other than liver, or expression in liver tissue relative to a reference UGT1A or UGT1E polypeptide. Similarly, expression of polymorphisms in UGT1F, which is normally expressed in liver, kidney and skin, could be assayed in each of these tissues and the relative levels of expression compared to a reference UGT1F polypeptide.

Substrate screening assay. Substrate screening assays are used to determine the metabolic activity of a UGT1 protein or peptide fragment on a substrate. Many suitable assays are known in the art, including the use of primary or cultured cells, genetically modified cells (e.g., where DNA encoding the UGT1 polymorphism to be studied is introduced into the cell within an artificial construct), cell-free systems, e.g. microsomal preparations or recombinantly produced enzymes in a suitable buffer, or in animals, including human clinical trials (see, e.g., Burchell et al. (1995) *Life Sci.* 57:1819–1831, specifically incorporated herein by reference. Where genetically modified cells are used, since most cell lines do not express UGT1 activity (liver cells lines being the exception), introduction of artificial construct for expression of the UGT1 polymorphism into many human and non-human cell lines does not require additional modification of the host to inactivate endogenous UGT1 expression/activity. Clinical trials may monitor serum, urine, etc. levels of the substrate or its metabolite(s).

Typically a candidate substrate is input into the assay system, and the conversion to a metabolite is measured over time. The choice of detection system is determined by the substrate and the specific assay parameters. Assays are conventionally run, and will include negative and positive controls, varying concentrations of substrate and enzyme, etc.

Genotyping: UGT1 genotyping is performed by DNA or RNA sequence and/or hybridization analysis of any convenient sample from a patient, e.g. biopsy material, blood sample (serum, plasma, etc.), buccal cell sample, etc. A nucleic acid sample from an individual is analyzed for the presence of polymorphisms in UGT1, particularly those that affect the activity or expression of UGT1. Specific sequences of interest include any polymorphism that leads to changes in basal expression in one or more tissues, to changes in the modulation of UGT1 expression by modifiers, or alterations in UGT1 substrate specificity and/or activity.

Linkage Analysis: Diagnostic screening may be performed for polymorphisms that are genetically linked to a phenotypic variant in UGT1 activity or expression, particularly through the use of microsatellite markers or single nucleotide polymorphisms (SNP). The microsatellite or SNP polymorphism itself may not phenotypically expressed, but is linked to sequences that result in altered activity or expression. Two polymorphic variants may be in linkage disequilibrium, i.e. where alleles show non-random associations between genes even though individual loci are in Hardy-Weinberg equilibrium.

Linkage analysis may be performed alone, or in combination with direct detection of phenotypically evident polymorphisms. The use of microsatellite markers for genotyping is well documented. For examples, see Mansfield et al. (1994) *Genomics* 24:225–233; and Ziegle et al. (1992) *Genomics* 14:1026–1031. The use of SNPs for genotyping is illustrated in Underhill et al. (1996) *Proc Natl Acad Sci U S A* 93:196–200.

Transgenic animals. The subject nucleic acids can be used to generate genetically modified non-human animals or site specific gene modifications in cell lines. The term "transgenic" is intended to encompass genetically modified animals having a deletion or other knock-out of UGT1 gene activity, having an exogenous UGT1 gene that is stably transmitted in the host cells, or having an exogenous UGT1 promoter operably linked to a reporter gene. Transgenic animals may be made through homologous recombination, where the UGT1 locus is altered. Alternatively, a nucleic acid construct is randomly integrated into the genome. Vectors for stable integration include plasmids, retroviruses and other animal viruses, YACs, and the like. Of interest are transgenic mammals, e.g. cows, pigs, goats, horses, etc., and particularly rodents, e.g. rats, mice, etc.

Genetically Modified Cells. Primary or cloned cells and cell lines are modified by the introduction of vectors comprising UGT1 gene polymorphisms. The gene may comprise one or more variant sequences, preferably a haplotype of commonly occurring combinations. In one embodiment of the invention, a panel of two or more genetically modified cell lines, each cell line comprising a UGT2B4 polymorphism, are provided for substrate and/or expression assays. The panel may further comprise cells genetically modified with other genetic sequences, including polymorphisms, particularly other sequences of interest for pharmacogenetic screening, e.g. UGT1, other UGT2 sequences, cytochrome oxidase polymorphisms, etc.

Vectors useful for introduction of the gene include plasmids and viral vectors, e.g. retroviral-based vectors, adenovirus vectors, etc. that are maintained transiently or stably in mammalian cells. A wide variety of vectors can be employed for transfection and/or integration of the gene into the genome of the cells. Alternatively, micro-injection may be employed, fusion, or the like for introduction of genes into a suitable host cell.

Genotyping Methods

The effect of a polymorphism in the UGT1 gene sequence on the response to a particular substrate or modifier of UGT1 is determined by in vitro or in vivo assays. Such assays may include monitoring the metabolism of a substrate during clinical trials to determine the UGT1 enzymatic activity, specificity or expression level. Generally, in vitro assays are useful in determining the direct effect of a particular polymorphism, while clinical studies will also detect an enzyme phenotype that is genetically linked to a polymorphism.

The response of an individual to the substrate or modifier can then be predicted by determining the UGT1 genotype, with respect to the polymorphism. Where there is a differential distribution of a polymorphism by racial background, guidelines for drug administration can be generally tailored to a particular ethnic group.

The basal expression level in different tissue may be determined by analysis of tissue samples from individuals typed for the presence or absence of a specific polymorphism. Any convenient method may be use, e.g. ELISA, RIA, etc. for protein quantitation, northern blot or other hybridization analysis, quantitative RT-PCR, etc. for mRNA quantitation. The tissue specific expression is correlated with the genotype.

The alteration of UGT1 expression in response to a modifier is determined by administering or combining the candidate modifier with an expression system, e.g. animal, cell, in vitro transcription assay, etc. The effect of the modifier on UGT1 transcription and/or steady state mRNA levels is determined. As with the basal expression levels, tissue specific interactions are of interest. Correlations are made between the ability of an expression modifier to affect UGT1 activity, and the presence of the provided polymorphisms. A panel of different modifiers, cell types, etc. may be screened in order to determine the effect under a number of different conditions.

A UGT1 polymorphism that results in altered enzyme activity or specificity is determined by a variety of assays known in the art. The enzyme may be tested for metabolism of a substrate in vitro, for example in defined buffer, or in cell or subcellular lysates, where the ability of a substrate to be metabolized by UGT1 under physiologic conditions is determined. Where there are not significant issues of toxicity from the substrate or metabolite(s), in vivo human trials may be utilized, as previously described.

The genotype of an individual is determined with respect to the provided UGT1 gene polymorphisms. The genotype is useful for determining the presence of a phenotypically evident polymorphism, and for determining the linkage of a polymorphism to phenotypic change.

A number of methods are available for analyzing nucleic acids for the presence of a specific sequence. Where large amounts of DNA are available, genomic DNA is used directly. Alternatively, the region of interest is cloned into a suitable vector and grown in sufficient quantity for analysis. The nucleic acid may be amplified by conventional techniques, such as the polymerase chain reaction (PCR), to provide sufficient amounts for analysis. The use of the polymerase chain reaction is described in Saiki et al. (1985) *Science* 230:1350–1354, and a review of current techniques may be found in Sambrook et al *Molecular Cloning: A Laboratory Manual*, CSH Press 1989, pp.14.2–14.33. Amplification may be used to determine whether a polymorphism is present, by using a primer that is specific for the polymorphism. Alternatively, various methods are known in the art that utilize oligonucleotide ligation as a means of detecting polymorphisms, for examples see Riley et al. (1990) *Nucleic Acids Res* 18:2887–2890; and Delahunty et al. (1996) *Am J Hum Genet* 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. 32P, 35S, 3H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods. Hybridization with the variant sequence may also be used to determine its presence, by Southern blots, dot blots, etc. The hybridization pattern of a control and variant sequence to an array of oligonucleotide probes immobilized on a solid support, as described in U.S. Pat. No. 5,445,934, or in WO95/35505, may also be used as a means of detecting the presence of variant sequences. Single strand conformational polymorphism (SSCP) analysis, denaturing gradient gel electrophoresis (DGGE), mismatch cleavage detection, and heteroduplex analysis in gel matrices are used to detect conformational changes created by DNA sequence variation as alterations in electrophoretic mobility. Alternatively, where a polymorphism creates or destroys a recognition site for a restriction endonuclease (restriction fragment length polymorphism, RFLP), the sample is digested with that endonuclease, and the products size fractionated to determine whether the fragment was digested. Fractionation is performed by gel or capillary electrophoresis, particularly acrylamide or agarose gels.

In one embodiment of the invention, an array of oligonucleotides are provided, where discrete positions on the array are complementary to one or more of the provided polymorphic sequences, e.g. oligonucleotides of at least 12 nt, frequently 20 nt, or larger, and including the sequence flanking the polymorphic position. Such an array may comprise a series of oligonucleotides, each of which can specifically hybridize to a different polymorphism. For examples of arrays, see Hacia et al. (1996) *Nat Genet* 14:441–447 and DeRisi et al. (1996) *Nat Genet* 14:457–460. Arrays of interest may further comprise sequences, including polymorphisms, of other genetic sequences, particularly other sequences of interest for pharmacogenetic screening, e.g. UGT1, other UGT2 sequences, cytochrome oxidase polymorphisms, etc.

The genotype information is used to predict the response of the individual to a particular UGT1 substrate or modifier. Where an expression modifier inhibits UGT1 expression, then drugs that are a UGT1 substrate will be metabolized more slowly if the modifier is co-administered. Where an expression modifier induces UGT1 expression, a co-administered substrate will typically be metabolized more rapidly. Similarly, changes in UGT1 activity will affect the metabolism of an administered drug. The pharmacokinetic effect of the interaction will depend on the metabolite that is produced, e.g. a prodrug is metabolized to an active form, a drug is metabolized to an inactive form, an environmental compound is metabolized to a toxin, etc. Consideration is given to the route of administration, drug-drug interactions, drug dosage, etc.

EXAMPLES

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g., amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLE: IDENTIFICATION OF UGT1 POLYMORPHISMS

Materials and Methods

DNA Samples. Blood specimens were collected from approximately 48 individuals after obtaining informed consent. All samples were stripped of personal identifiers to maintain confidentiality. Genomic DNA was isolated from these samples using standard techniques. Genomic DNA was stored either as a concentrated solution, or in a dried form in microtiter plates.

PCR amplifications. The primers used to amplify all exons are shown in Table 2, and were designed with NBI's Oligo version 5.0 program.

Publicly available genomic sequences were used as references. Twenty-five nanograms of genomic DNA were amplified in the primary amplifications using the Perkin Elmer GeneAmp PCR kit according to the manufacturer's instructions in 25 $\mu$l reactions with AmpliTaq Gold DNA polymerase. Reactions contained 25 mM MgCl2 and 0.2 $\mu$M of each primer. Thermal cycling was performed using a GeneAmp PCR System 9600 PCR machine (Perkin Elmer), utilizing a touch-down PCR protocol. The protocol, unless indicated otherwise in Table 3, consisted of an initial incubation of 95° C. for 10 min, followed by eight cycles of 95° C. for 20 sec, 66° C. (minus 1° C. per cycle) for 15 sec, 72° C. for 2 min, and twenty-seven cycles of 95° C. for 20 sec, 54° C. for 15 sec, 72° C. for 2 min, and one final extension step of 72° C. for 10 min.

For the secondary PCR reactions, one microliter of each primary PCR reaction was re-amplified using the secondary PCR primers, also listed in Table 2. The thermal cycling profile that was used for the primary PCR for an exon was used for the secondary PCR.

TABLE 3

Cycling Profile Modifications

| Exon | Primary PCR | Secondary PCR |
|---|---|---|
| 1E | Touch-Down PCR step: 8 cycles 64 C (minus 1 C per cycle), for 15 sec Total Number of cycles: 35 | same as Primary PCR |
| 1F | Touch-Down PCR step: 10 cycles 64 C (minus 1 C per cycle), for 15 sec Total Number of cycles: 35 | same as Primary PCR |
| 1G | Touch-Down PCR step: 7 cycles 64 C (minus 1 C per cycle), for 15 sec Total Number of cycles: 35 | same as Primary PCR |
| 1H | Touch-Down PCR step: 10 cycles 66 C (minus 1 C per cycle), for 15 sec Total Number of cycles: 35 | same as Primary PCR |

DNA sequencing. PCR products from 48 individuals, approximately one-third representing each of the 3 major racial groups (see above), were prepared for sequencing by treating 8 $\mu$L of each PCR product with 0.15 $\mu$L of exonuclease I (1.5 U/reaction), 0.3 $\mu$L of Shrimp Alkaline Phosphatase (0.3 U/reaction), q.s. to 10 $\mu$L with MilliQ water, and incubated at 37° C. for 15 min, followed by 72° C. for 15 min. Cycle sequencing was performed on the GeneAmp PCR System 9600 PCR machine (Perkin Elmer) using the ABI Prism dRhodamine Terminator Cycle Sequencing Ready Reaction Kit according to the manufacturer's directions, with the following changes: (1) 2 $\mu$L of dRhodamine terminator premix, instead of 8 $\mu$L; and (2) 10% (v/v) Dimethylsulfoxide was added to each individual nucleotide. The oligonucleotide primers (unlabeled), at 3 picomoles per reaction, used for the sequencing reactions are listed in Table 4. Sequencing reactions, with a final volume of 5 $\mu$L, were subjected to 30 cycles at 96° C. for 20 sec, 50° C. for 5 sec, and 60° C. for 4 min, followed by ethanol precipitation. After decanting the ethanol, samples were

TABLE 2

PCR Primers. (Ex = Exon)

| EX | FORWARD PRIMER | | REVERSE PRIMER | |
|---|---|---|---|---|
| | PRIMARY PCR AMPLIFICATION | | | |
| 1A | TGGTGTATCGATTGGTTTT | (SEQ ID NO: 19) | CATATATCTGGGGCTAGTTAATC | (SEQ ID NO: 20) |
| 1C | ACAAGGTAATTAAGATGAAGAAAGCA | (SEQ ID NO: 21) | ACCTGAGATAGTGGCTTCCT | (SEQ ID NO: 22) |
| 1D | TTTGTCTTCCAATTACATGC | (SEQ ID NO: 23) | AGTAGATATGGAAGCACTTGTAAG | (SEQ ID NO: 24) |
| 1E | TCTCAGTGACAAGGTAATTAAGAC | (SEQ ID NO: 25) | CATTGATTGGATAAAGGCA | (SEQ ID NO: 26) |
| 1F | AATTTGGGTTCTTACATATCAA | (SEQ ID NO: 27) | GAGTGAGGGAGGACAGAG | (SEQ ID NO: 28) |
| 1G | ATAAGTACACGCCTTCTTTTG | (SEQ ID NO: 29) | GCTGCTTTATACAATTTGCTAC | (SEQ ID NO: 30) |
| 1H | CGCCTACGTATCATAGCAGTTA | (SEQ ID NO: 31) | GGAAAGAAATTTGAAATGCAAC | (SEQ ID NO: 32) |
| 1J | TCTTTCCGCCTACTGTATCA | (SEQ ID NO: 33) | TTCAAGAAGGGCAGTTTTAT | (SEQ ID NO: 34) |
| | SECONDARY PCR AMPLIFICATION | | | |
| 1A | CTCTGGCAGGAGCAAAG | (SEQ ID NO: 35) | ATACACACCTGGGATAGTGG | (SEQ ID NO: 36) |
| 1C | GGTAATTAAGATGAAGAAAGCA | (SEQ ID NO: 37) | CTGAGATAGTGGCTTCCTG | (SEQ ID NO: 38) |
| 1D | GTGGCTCAATGACAAGG | (SEQ ID NO: 39) | ATATGGAAGCACTTGTAAGTAAA | (SEQ ID NO: 40) |
| 1E | TTAAGACGAAGGAAACAATTCT | (SEQ ID NO: 41) | ACCTGAGATAGTGGCTTCC | (SEQ ID NO: 42) |
| 1F | ATCAAAGGGTAAAATTCAGA | (SEQ ID NO: 43) | GGCAGTCCAAAAGAAATA | (SEQ ID NO: 44) |
| 1G | TTTTGAGGGCAGGTTCTA | (SEQ ID NO: 45) | AATGGGACAAATGTAAATGATA | (SEQ ID NO: 46) |
| 1H | TTCTCTCATGGCTCGCA | (SEQ ID NO: 47) | ATGTCAAATCACAATTCAGTAAGG | (SEQ ID NO: 48) |
| 1J | CCGCCTACTGTATCATAGCA | (SEQ ID NO: 49) | CAACGAAATGTCAAATCACAG | (SEQ ID NO: 50) | evaporated to dryness using a SpeedVac for roughly 15 min and were resuspended in 2 μl of loading buffer (5:1 deionized formamide:50 mM EDTA pH 8.0). The samples were then, heated to 94° C. for 2 min, and electrophoresed through 5.25% polyacrylamide/6M urea gels in an ABI Prism 377 DNA Sequencer according to the manufacturer's instructions for sequence determination. All sequences were determined from both the 5' and 3' (sense and antisense) direction.

Of the forty-eight samples, 38 polymorphisms were identified. The polymorphisms are described in Table 5 below.

TABLE 4

Sequencing Primers (No. = Polymorphism No.)

| No. | FORWARD PRIMER | | REVERSE PRIMER | |
|---|---|---|---|---|
| 1 | CTCTGGCAGGAGCAAAG | (SEQ ID NO: 51) | ACAGTGGGCAGAGACAG | (SEQ ID NO: 52) |
| 2 | GTGGTTTATTCCCCGTAT | (SEQ ID NO: 53) | ATACACACCTGGGATAGTGG | (SEQ ID NO: 54) |
| 3–5 | GGTAATTAAGATGAAGAAAGCA | (SEQ ID NO: 55) | GAAATGGCATAGGTTGTC | (SEQ ID NO: 56) |
| 6 | GGCCACACTCAACTGTA | (SEQ ID NO: 57) | CTCAAAAAAAACACAGTAGG | (SEQ ID NO: 58) |
| 7, 8 | ACTTTTTCTGCCCCTTAT | (SEQ ID NO: 59) | ATATGGAAGCACTTGTAAGTAAA | (SEQ ID NO: 60) |
| 9–12 | TTAAGACGAAGGAAACAATTCT | (SEQ ID NO: 61) | AATGGCATACGTTGTCA | (SEQ ID NO: 62) |
| 13, 14 | AGAATGGCAATTATGAACA | (SEQ ID NO: 63) | TGTGTGCCCTTAAAGTCT | (SEQ ID NO: 64) |
| 15–17 | AGAATGGCAATTATGAACA | (SEQ ID NO: 65) | ACCTGAGATAGTGGCTTCC | (SEQ ID NO: 66) |
| 18–24 | CTCTGGC T CTGTCCTAC* | (SEQ ID NO: 67) | ACCTGAGATAGTGGCTTCC | (SEQ ID NO: 68) |
| 25 | ATCAAAGGGTAAAATTCAGA | (SEQ ID NO: 69) | CAGCAGCTTGTCACCTAC | (SEQ ID NO: 70) |
| 26 | AATTTGCTTTTGAAAGAATC | (SEQ ID NO: 71) | GGTAGGCCCAAATACTCA | (SEQ ID NO: 72) |
| 27, 28 | AATTTGCTTTTGAAAGAATC | (SEQ ID NO: 73) | GGCAGTCCAAAAGAAATA | (SEQ ID NO: 74) |
| 29, 30 | TTTTGAGGGCAGGTTCTA | (SEQ ID NO: 75) | CACCTCTGGCATGACTAC | (SEQ ID NO: 76) |
| 31, 32 | TTGCAGGAGTTTGTTTAAT | (SEQ ID NO: 77) | AATGGGACAAATGTAAATGATA | (SEQ ID NO: 78) |
| 33 | CATTGCAGGAGTTTGTTTA | (SEQ ID NO: 79) | CATCTGAGAACCCTAAGAGA | (SEQ ID NO: 80) |
| 34 | AGAAATAGCCTCTGAAATTC | (SEQ ID NO: 81) | ATGTCAAATCACAATTCAGTAAGG | (SEQ ID NO: 82) |
| 35 | CCGCCTACTGTATCATAGCA | (SEQ ID NO: 83) | GAGTGTACGAGGTTGAGTAAG | (SEQ ID NO: 84) |
| 36–38 | ATTTTGCCAGTATCTTTTAG | (SEQ ID NO: 85) | CAACGAAATGTCAAATCACAG | (SEQ ID NO: 86) |

*Note polymorphism in primer. The reference sequence has a "C" at the highlighted position.

TABLE 5

UGT1 polymorphisms. Amino acid changes numbered from first methionine for that exon (Ex).

| No | Ex | Ntd | AA | SEQUENCE | (SEQ ID NO: ) |
|---|---|---|---|---|---|
| 1 | 1A | G 227 A | Gly 71 Arg | CATCAGAGAC A GAGCATTTTACACCTT | (SEQ ID NO: 87) |
| 2 | 1A | T → C | Ser 250 Pro | GGACCTATTGAGC C CTGCATCTGTCT | (SEQ ID NO: 88) |
| 3 | 1C | T → C | Trp 11 Arg | GGTTCCCCTGCCG C GGCTGGCCACA | (SEQ ID NO: 89) |
| 4 | 1C | G → A | | GCCCTGGGCTGA A AGTGGAAAG | (SEQ ID NO: 90) |
| 5 | 1C | T → C | Val 47 Ala | ATGCGGGAGG C CTTGCGGGAGCT | (SEQ ID NO: 91) |
| 8 | 1C | A → G | | CTCTGCGCGGC G GTGCTGGCTAAG | (SEQ ID NO: 92) |
| 7 | 1D | G → A | | TACCCCAGGCC A ATCATGCCCAACA | (SEQ ID NO: 93) |
| 8 | 1D | C → T | Intronic | TCCAGGCAAAA T ACTTTTTAAAAAATG | (SEQ ID NO: 94) |
| 9 | 1E | T → C | Leu 48 Ser | AGCATGCGGGAGGCCT C GCGGGAA | (SEQ ID NO: 95) |
| 10 | 1E | C → G | Asp 50 Glu | GCGGGA G CTCCATGCGAGAGG | (SEQ ID NO: 96) |
| 11 | 1E | T → C | Leu 83 Pro | TGGTGGTCCTCACCC C GGAGGTGAA | (SEQ ID NO: 97) |
| 12 | 1E | A → G | | TACATCAAAGA G GAGAACTTTTTCAC | (SEQ ID NO: 98) |
| 13 | 1E | C → A | His 142 Asn | TGATCAGGCACCTG A ATGCTACTTCC | (SEQ ID NO: 99) |
| 14 | 1E | C → G | Ala 158 Gly | ACCTCTGCG G GGCGGTGCTGG | (SEQ ID NO: 100) |
| 15 | 1E | C → T | | AAGAACATGCT T TACCCTCTGGC | (SEQ ID NO: 101) |
| 16 | 1E | C → T | | CTCTGGC T CTGTCCTACC | (SEQ ID NO: 102) |
| 17 | 1E | C → T | | TCCTACCTTTGC T ATGCTGTTTCT | (SEQ ID NO: 103) |
| 18 | 1E | C → A | Leu 248 Ile | TGTCAGTGGTGGAT A TT | (SEQ ID NO: 104) |
| 19 | 1E | G → C | Val 249 Leu | GGTGGATCTT C TCAGC | (SEQ ID NO: 105) |
| 20 | 1E | C → T | His 251 Tyr | TCAGC T ATGCATC | (SEQ ID NO: 106) |
| 21 | 1E | T → C | Ser 253 Phe | GCATC C GTGTGGCTGTTCCGA | (SEQ ID NO: 107) |
| 22 | 1E | 0 → C | Gly 259 Arg | TGGCTGTTCCGA C GGGACTT | (SEQ ID NO: 108) |
| 23 | 1E | T → C | | GGGACTT C GTGATGGA | (SEQ ID NO: 109) |
| 24 | 1E | T → C | | GTGATGGA C TACCCCAGGCCGAT | (SEQ ID NO: 110) |
| 25 | 1F | T → G | Ser 7 Ala | CCTGCCTCCTTCGC G CATTTCAGAG | (SEQ ID ND:111) |
| 26 | 1F | A → G | | GCGATCATTCCT G ACTGCTCCTCAG | (SEQ ID NO: 112) |
| 27 | 1F | A → G | Thr 181 Ala | CCCTGGAGCAT G CATTCAGCAG | (SEQ ID NO: 113) |
| 28 | 1F | A → C | Arg 184 Ser | CATTCAGCAG C AGCCCAGACCCT | (SEQ ID NO: 114) |
| 29 | 1G | T → G | | TACTTCTTCCAC G TACTATATTA | (SEQ ID NO: 115) |
| 30 | 1G | C → A | | GGCCTCCTTCC A CTATATGTGTGT | (SEQ ID NO: 116) |
| 31 | 1G | T → C | Trp 208 Arg | GGAGAGAGTA C GGAACCACAT | (SEQ ID NO: 117) |
| 32 | 1G | G → A | | TCAATTTGGTT A TTGCGAACTGA | (SEQ ID NO: 118) |
| 33 | 1H | G → C | Gly 173 Ala | CAGGGGAATAG C TTGCCACTAT | (SEQ ID NO: 119) |
| 34 | 1H | A → G | | TGTTGCGAAC G GACTTTGTTTTGG | (SEQ ID NO: 120) |
| 35 | 1J | G → A | | TTCACCATGCA A TCGGTGGTGG | (SEQ ID NO: 121) |
| 36 | 1J | C → T | | CTAGAAATAGC T TCTGAAATTCTCC | (SEQ ID NO: 122) |
| 37 | 1J | C → A | Leu 212 Ile | CGGCATATGAT A TCTACAGTCACA | (SEQ ID NO: 123) |
| 38 | 1J | T → C | | TCAATTTGGTTG C TGCGAACGGAC | (SEQ ID NO: 124) |

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated UGT1 polynucleotide comprising a nucleic acid sequence selected from the group consisting of: (a) a nucleic acid sequence comprising SEQ ID NO:98; (b) a nucleic acid sequence comprising at least 20 contiguous nucleotides of a nucleic acid sequence selected from the group consisting of SEQ ID NO:88, SEQ ID NO:90, SEQ ID NO:95, SEQ ID NO:96, SEQ ID NO:97, SEQ ID NO:98, SEQ ID NO:101, SEQ ID NO:102, SEQ ID NO:103, SEQ ID NO:109, SEQ ID NO:108, SEQ ID NO:111, SEQ ID NO:112, SEQ ID NO:115, SEQ ID NO:116, SEQ ID NO:118, SEQ ID NO:119, SEQ ID NO:121, SEQ ID NO:122, SEQ ID NO:123, and SEQ ID NO:124; and (c) a nucleic acid sequence that is fully complementary to a nucleic acid sequence of (a) or (b).

2. A nucleic acid probe for the detection of a UGT1 locus, said probe comprising at least one polynucleotide of Claim 1.

3. A nucleic acid probe according to claim 2, wherein said probe is conjugated to a detectable marker.

4. An array of oligonucleotides comprising:
two or more probes for the detection of a UGT 1 locus, said probes comprising at least one polynucleotide of Claim 1.

5. An isolated UGTL polynucleotide having a polymorphism, wherein said polyrnicleotide comprises a polynucleotide selected from the group consisting of:

(a) SEQ ID NO: 1 with the exception that a C nucleotide is substituted for a T nucleotide at position 748 of SEQ ID NO: 1, (b) SEQ ID NO: 3 with the exception that an A nucleotide is substituted for a G nucleotide at position 81 of SEQ ID NO: 3;

(c) SEQ ID NO: 7 with the exception that an A nucleotide is substituted for a C nucleotide at position 742 of SEQ ID NO: 7;

(d) SEQ ID NO: 7 with the exception that a T nucicocide is substituted far a C nucleotide at position 143 of SEQ ID NO: 7;

(e) SEQ ID NO: 7 with the exception that a G nucleotide is substituted for a C nucleotide at position 745 of SEQ ID NO: 7;

(f) SEQ ID NO: 7 with the exception that a C nucleotide is substituted for a T nucleotide at position 188 of SEQ ID NO: 7;

(g) SEQ ID NO: 7 with the exception that a G nucleotide is substituted for an A nucleotide at position 213 of SEQ ID NO: 7;

(h) SEQ ID NO: 7 with the exception that a T nucleotide is substituted for a C nucleotide at position 645 of SEQ ID NO: 7;

(i) SEQ ID NO: 7 with the exception that a T nucleotide is substituted for a C nucleotide at position 657 of SEQ ID NO: 7;

(j) SEQ ID NO: 7 with the exception that a T nucleotide is substituted for a C nucleotide at position 673 of SEQ ID NO: 7;

(k) SEQ ID NO: 7 with the exception that a C nucleotide is substituted for a G nucleotide at position 745 of SEQ ID NO: 7;

(l) SEQ ID NO: 7 with the exception that a T nucleotide is substituted for a C nucleotide at position 751 of SEQ ID NO: 7;

(m) SEQ ID NO: 7 with the exception that a C nucleotide is substituted for a G nucleotide at position 775 of SEQ ID NO: 7;

(n) SEQ ID NO: 7 with the exception that a C nucleotide is substituted for a T nucleotide at position 783 of SEQ ID NO: 7;

(o) SEQ ID NO: 9 with the exception that a G nucleotide is substituted for a T nucleotide at position 19 of SEQ ID NO: 9;

(p) SEQ ID NO: 9 with the exception that a G nucleotide is substituted for an A nucleotide at position 315 of SEQ ID NO: 9;

(q) SEQ ID NO: 11 with the exception that a G nucleotide is substituted for a T nucleotide at position 108 of SEQ ID NO: 11;

(r) SEQ ID NO: 11 with the exception that an A nucleotide is substituted for a C nucleotide at position 197 of SEQ ID NO: 11;

(s) SEQ ID NO: 11 with the exception that a C nucleotide is substituted for a T nucleotide at position 786 of SEQ ID NO: 11;

(t) SEQ ID NO: 11 with the exception that an A nucleotide is substituted for a G nucleotide at position 920 of SEQ ID NO: 11;

(u) SEQ ID NO: 13 with the exception that a C nucleotide is substituted for a G nucleotide at position 518 of SEQ ID NO: 13;

(v) SEQ ID NO: 13 with the exception that a G nucleotide is substituted for an A nucleotide at position 765 of SEQ ID NO: 13;

(w) SEQ ID NO: 15 with the exception that an A nucleotide is substituted for a G nucleotide at position 30 of SEQ ID NO: 15;

(x) SEQ ID NO: 15 with the exception that a T nucleotide is substituted for a C nucleotide at position 597 of SEQ ID NO: 15;

(y) SEQ ID NO: 15 with the exception that an A nucleotide is substituted for a C nucleotide at position 634 of SEQ ID NO: 15;

(z) SEQ ID NO: 15 with the exception that a C nucleotide is substituted for a T nucleotide at position 661 of SEQ ID NO: 15, and;

(aa) a nucleic acid sequence that is fully complementary to a nucleic acid sequence of (a), (b), (c), (d), (e), (f), (g), (h), (i), (j), (k), (l), (m), (n), (o), (p), (q), (r), (s), (t), (u), (v), (w), (x), (y), or (z).

6. An isolated UGT1 polynucleotide wherein said polynucleotide comprises a nucleic acid selected from the group consisting of:
   (a) a nucleic acid molecule that comprises a thymine at position 657 of SEQ ID NO: 7 and at least 50 contiguous bases of SEQ ID NO:7 immediately adjacent to said position 657;
   (b) a nucleic acid molecule that comprises a cytosine at position 745 of SEQ ID NO: 7 and at least 50 contiguous bases of SEQ ID NO:7 immediately adjacent to said position 745;
   (c) a nucleic acid molecule that comprises a cytosine at position 783 of SEQ ID NO: 7 and at least 50 contiguous bases of SEQ ID NO:7 immediately adjacent to said position 783; and,
   (d) a nucleic acid molecule which is fully complementary to a nucleic acid molecule of (a)–(c).

7. A method for detecting in an individual a UGT1 polynucleotide, the method comprising:
   (a) obtaining a nucleic acid sample that has been isolated from an individual; and
   (b) contacting said nucleic acid sample with a UGT1 polynucleotide probe, wherein said UGT1 polynucleotide probe comprises a nucleic acid sequence selected from the group consisting of:
      (i) a nucleic acid sequence comprising SEQ ID NO:98;
      (ii) a nucleic acid sequence comprising at least 20 contiguous nucleotides of a nucleic acid sequence selected from the group consisting of SEQ ID NO:88, SEQ ID NO:90, SEQ ID NO:95, SEQ ID NO:96, SEQ ID NO:97, SEQ ID NO:98, SEQ ID NO:101, SEQ ID NO:102, SEQ ID NO:103, SEQ ID NO:108, SEQ ID NO:109, SEQ ID NO:111, SEQ ID NO:112, SEQ ID NO:115, SEQ ID NO:116, SEQ ID NO:118, SEQ ID NO:119, SEQ ID NO:121, SEQ ID NO:122, SEQ ID NO:123, and SEQ ID NO:124; and
      (iii) a nucleic acid sequence that is fully complementary to a nucleic acid sequence of (i)—(ii); and,
   (c) detecting specific hybridization between said polynucleotide probe and said nucleic acid sample as indicative of the presence of a UGT1 polynucleotide in said nucleic acid sample.

8. A method according to Claim 7, wherein said contacting step comprises contacting the said nucleic acid sample of said individual with an array of oligonucleotides comprising:
   two or more probes for the detection of a UGT1 locus, said probes comprising at least one UGT1 polynucleotide probe of Claim 7.

9. The method of Claim 7, wherein said nucleic acid sample is a genomic DNA sample.

10. The method of Claim 7, wherein said nucleic acid sample is an RNA sample.

* * * * *